(12) United States Patent
Suri

(10) Patent No.: US 7,417,164 B2
(45) Date of Patent: Aug. 26, 2008

(54) FLUORESCENT DYES FOR USE IN GLUCOSE SENSING

(75) Inventor: Jeff T. Suri, Rancho Santa Margarita, CA (US)

(73) Assignee: Glumetrics Inc., Irvine, CA (US)

( * ) Notice: Subject to any disclaimer, the term of this patent is extended or adjusted under 35 U.S.C. 154(b) by 0 days.

(21) Appl. No.: 11/782,553

(22) Filed: Jul. 24, 2007

(65) Prior Publication Data

US 2008/0027245 A1    Jan. 31, 2008

Related U.S. Application Data

(60) Provisional application No. 60/833,081, filed on Jul. 25, 2006.

(51) Int. Cl.
*C07F 9/02* (2006.01)
*C07F 9/38* (2006.01)
*C07C 311/29* (2006.01)
*C07C 309/24* (2006.01)

(52) U.S. Cl. ............... 562/31; 564/15; 564/83; 562/14; 562/35; 562/43; 562/44; 562/430; 600/316; 600/317; 436/95

(58) Field of Classification Search ........... 564/15, 564/83; 562/14, 31, 35, 43, 44, 430; 600/316, 600/317; 436/95
See application file for complete search history.

(56) References Cited

U.S. PATENT DOCUMENTS

| 5,137,833 | A | 8/1992 | Russell |
| 5,503,770 | A | 4/1996 | James et al. |
| 5,512,246 | A | 4/1996 | Russell et al. |
| 5,763,238 | A | 6/1998 | James et al. |
| 6,002,954 | A | 12/1999 | Van Antwerp et al. |
| 6,319,540 | B1 | 11/2001 | Van Antwerp et al. |
| 6,627,177 | B2 | 9/2003 | Singaram et al. |
| 6,653,141 | B2 | 11/2003 | Singaram et al. |
| 6,766,183 | B2 | 7/2004 | Walsh et al. |
| 6,794,195 | B2 | 9/2004 | Colvin, Jr. |
| 6,800,451 | B2 | 10/2004 | Daniloff et al. |
| 6,804,544 | B2 | 10/2004 | Van Antwerp et al. |
| 2004/0028612 | A1 | 2/2004 | Singaram et al. |
| 2006/0083688 | A1 | 4/2006 | Singaram et al. |

FOREIGN PATENT DOCUMENTS

WO    WO 02/46752 A2    6/2002

*Primary Examiner*—Peter G O'Sullivan
(74) *Attorney, Agent, or Firm*—Knobbe Martens Olson & Bear LLP

(57) ABSTRACT

A novel class of compounds that includes HPTS-Cys-MA, and methods of making them are disclosed herein. The class of compounds including HPTS-Cys-MA are useful as fluorescent dyes for analyte detection.

13 Claims, 9 Drawing Sheets

FLUORESCENT DYES FOR USE IN GLUCOSE SENSING

RELATED APPLICATIONS

This application claims the benefit of U.S. Provisional Application No. 60/833,081 filed Jul. 25, 2006 which is hereby incorporated by reference in its entirety.

BACKGROUND OF THE INVENTION

1. Field of the Invention

Novel fluorescent dyes are disclosed for use in analyte detection.

2. Description of the Related Art

Fluorescent dyes, including 8-hydroxypyrene-1,3,6-trislfonic acid (HPTS) and its derivatives, are known and have been used in analyte detection. See e.g., U.S. Pat. Nos. 6,653,141, 6,627,177, 5,512,246, 5,137,833, 6,800,451, 6,794,195, 6,804,544, 6,002,954, 6,319,540, 6,766,183, 5,503,770, and 5,763,238; and co-pending U.S. patent application Ser. Nos. 10/456,895 and 11/296,898; each of which is incorporated herein in its entirety by reference thereto.

SUMMARY OF THE INVENTION

Fluorescent dyes having the below generic structure are disclosed in accordance with embodiments of the present invention.

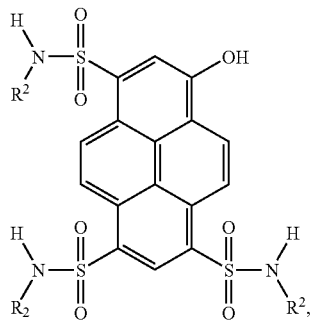

wherein:
$R^2$ is

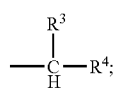

$R^3$ is $-(CH_2)_n-A^-M^+$,
   wherein n is 1-4,
   wherein $A^-$ is an anionic group selected from the group consisting of $SO_3^-$, $HPO_3^-$, $CO_2^-$ and

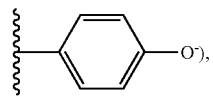

and
   wherein $M^+$ is a cationic group selected from the group consisting of $H^+$, an alkali metal ion, $Li^+$, $Na^+$, $K^+$, $Rb^+$, $Cs^+$, $Fr^+$, an onium ion and $NR_4^+$, wherein R is selected from the group consisting of alkyl, alkylaryl and aromatic groups);

$R^4$ is

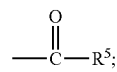

$R^5$ is selected from the group consisting of

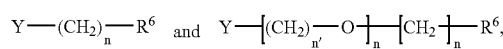

wherein n is equal to 1-10, n' is equal to 2-4, and Y is selected from the group consisting of NH and O;

$R^6$ is selected from the group consisting of $NHR^7$, $OR^7$ and $CO_2H$; and $R^7$ is H or an ethylenically unsaturated group selected from the group consisting of methacryloyl, acryloyl, styryl, acrylamido and methacrylamido.

Fluorescent dyes having the below generic structure are disclosed in accordance with preferred embodiments of the present invention.

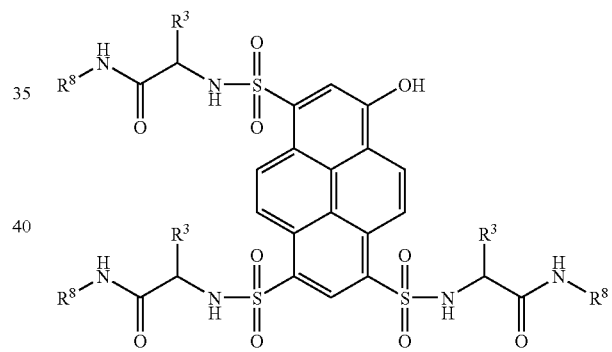

wherein:
$R^3$ is $-(CH_2)_n-A^-M^+$,
   wherein n is 1-4,
   wherein $A^-$ is an anionic group selected from the group consisting of $SO_3^-$, $HPO_3^-$, $CO_2^-$ and

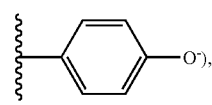

and
   wherein $M^+$ is a cationic group selected from the group consisting of $H^+$, an alkali metal ion, $Li^+$, $Na^+$, $K^+$, $Rb^+$, $Cs^+$, $Fr^+$, an onium ion and $NR_4^+$, wherein R is selected from the group consisting of alkyl, alkylaryl and aromatic groups);

$R^8$ is selected from the group consisting of

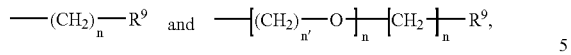

wherein n is equal to 1-10, n' is equal to 2-4;
$R^9$ is selected from the group consisting of $NHR^{10}$, $OR^{10}$ and $CO_2H$; and
$R^{10}$ is H or an ethylenically unsaturated group selected from the group consisting of methacryloyl, acryloyl, styryl, acrylamido and methacrylamido.

A fluorescent dye termed HPTS-Cys-MA (or HPTS-Tri-Cys-MA) having the below structure is disclosed in accordance with preferred embodiments of the present invention.

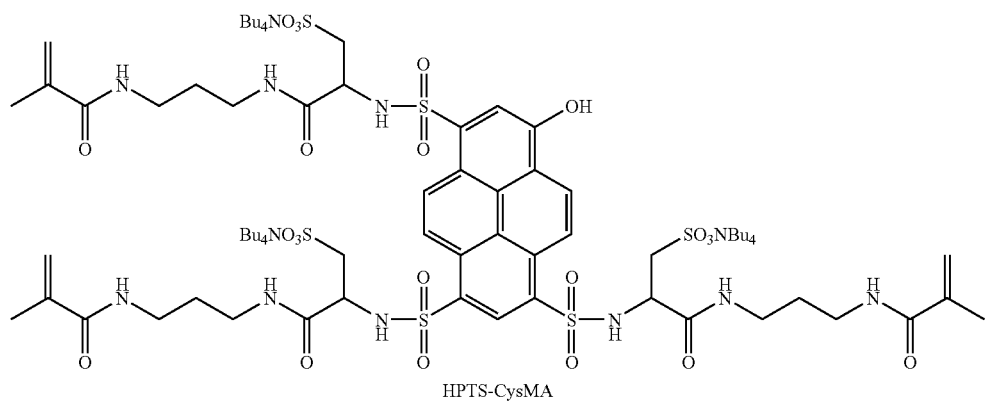

HPTS-CysMA

A glucose sensor is disclosed in accordance with another embodiment of the present invention, comprising the dyes disclosed herein (e.g., HPTS-Cys-MA) and a quencher comprising boronic acid, such as 3,3'-oBBV.

A first method of making the generic class of compounds to which HPTS-Cys-MA belongs is disclosed in accordance with another embodiment of the present invention. The method comprises the following steps:

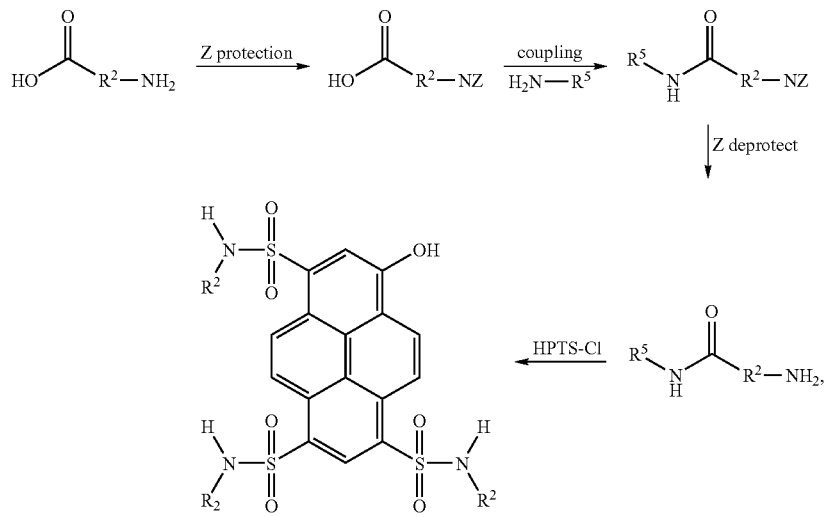

wherein:
R² is

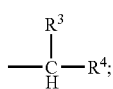

R³ is —(CH₂)ₙ—A⁻M⁺,
  wherein n is 1-4,
  wherein A⁻ is an anionic group selected from the group consisting of $SO_3^-$, $HPO_3^-$, $CO_2^-$ and

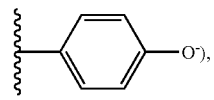

and
  wherein M⁺ is a cationic group selected from the group consisting of H⁺, an alkali metal ion, Li⁺, Na⁺, K⁺, Rb⁺, Cs⁺, Fr⁺, an onium ion and $NR_4^+$, wherein R is selected from the group consisting of alkyl, alkylaryl and aromatic groups);

R⁴ is

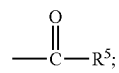

R⁵ is selected from the group consisting of

Y—(CH₂)ₙ—R⁶ and Y—[(CH₂)ₙ'—O]ₙ—[CH₂]ₙ—R⁶, wherein n is equal to 1-10, n' is equal to 2-4 and Y is selected from the group consisting of NH and O;
R⁶ is selected from the group consisting of NHR⁷, OR⁷ and CO₂H;
R⁷ is H or an ethylenically unsaturated group selected from the group consisting of methacryloyl, acryloyl, styryl, acrylamide and methacrylamido; and
Z is an amino protecting group selected from the group consisting of phthalimido, Boc and Fmoc).

A second method of making the generic class of compounds to which HPTS-Cys-MA belongs is disclosed in accordance with another embodiment of the present invention. The method comprises the steps of:

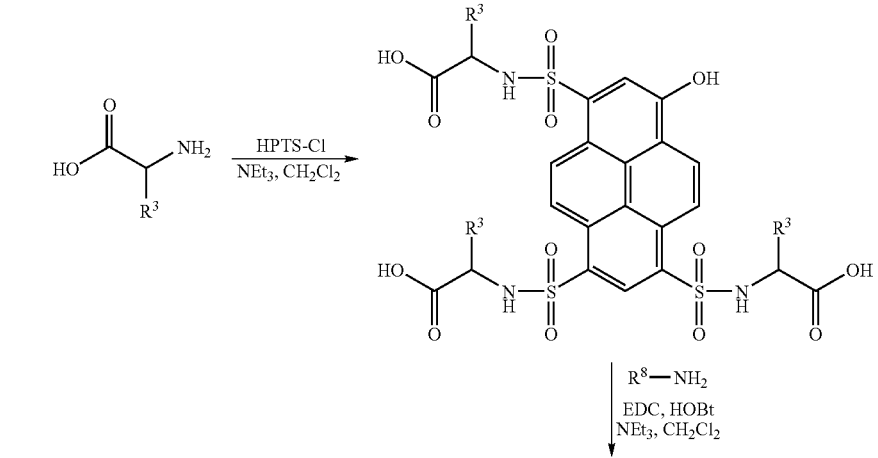

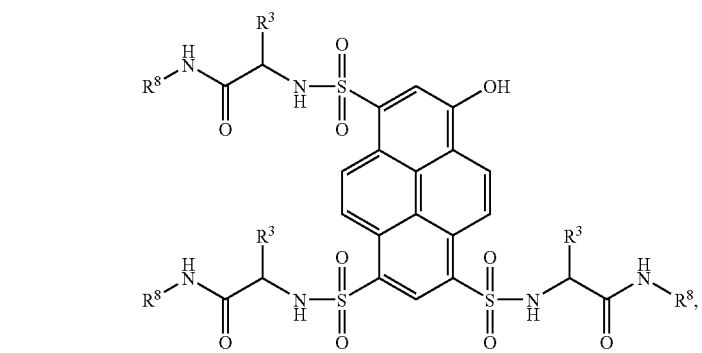

wherein:

$R^3$ is $-(CH_2)_n-A^-M^+$,
  wherein n is 1-4,
  wherein $A^-$ is an anionic group selected from the group consisting of $SO_3^-$, $HPO_3^-$, $CO_2^-$ and

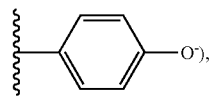

and
  wherein $M^+$ is a cationic group selected from the group consisting of $H^+$, an alkali metal ion, $Li^+$, $Na^+$, $K^+$, $Rb^+$, $Cs^+$, $Fr^+$, an onium ion and $NR_4^+$, wherein R is selected from the group consisting of alkyl, alkylaryl and aromatic groups);

$R^8$ is selected from the group consisting of $-(CH_2)_n-R^9$ and $-[(CH_2)_{n'}-O]_n[CH_2]_n-R^9$, wherein n is equal to 1-10, n' is equal to 2-4;
$R^9$ is selected from the group consisting of $NHR^{10}$, $OR^{10}$ and $CO_2H$; and
$R^{10}$ is H or an ethylenically unsaturated group selected from the group consisting of methacryloyl, acryloyl, styryl acrylamide and methacrylamido.

A specific method for making HPTS-Cys-MA is disclosed in accordance with another embodiment of the present invention. The method comprises the steps of making HPTS-CysOH as follows:

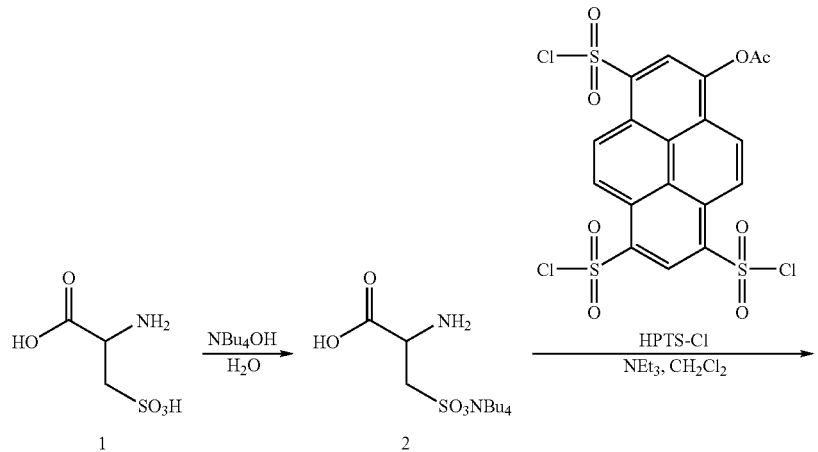

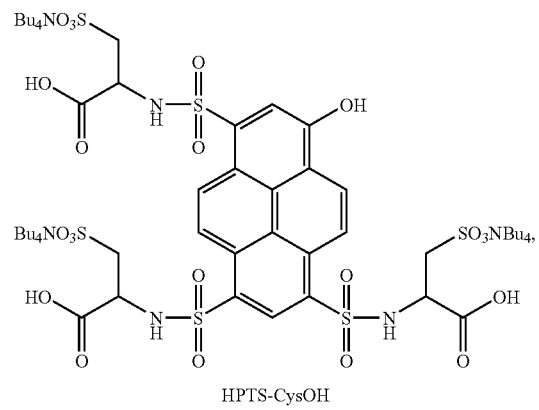

HPTS-CysOH and making HPTS-Cys-MA as follows:
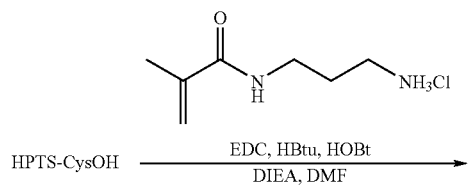
HPTS-CysOH $\xrightarrow{\text{EDC, HBtu, HOBt}}_{\text{DIEA, DMF}}$
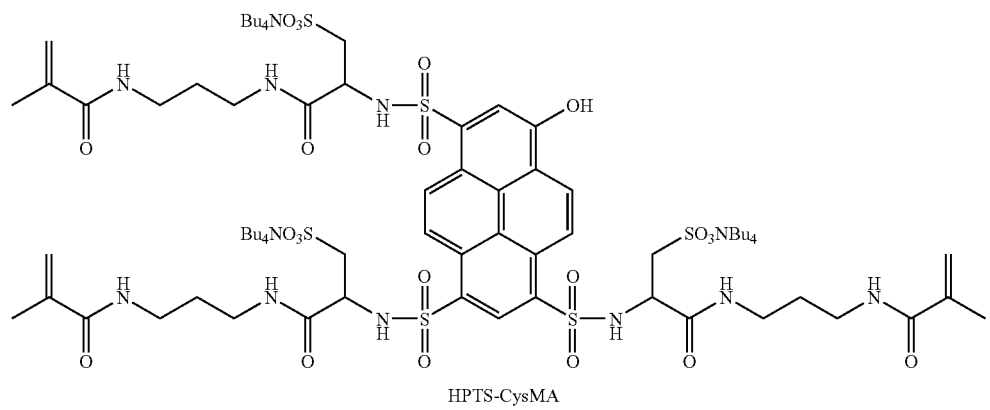
HPTS-CysMA
Another specific method for making HPTS-Cys-MA is disclosed in accordance with another embodiment of the present invention. The method comprises the steps of making:
a) TBCys as follows:
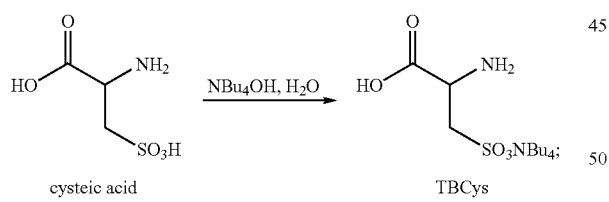
b) Phth acid as follows:
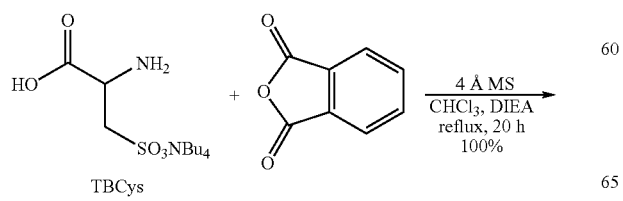
-continued
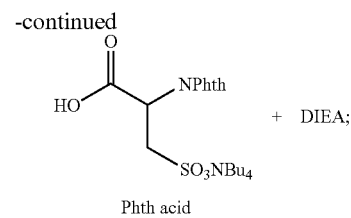
Phth acid
c) Phth MA as follows:
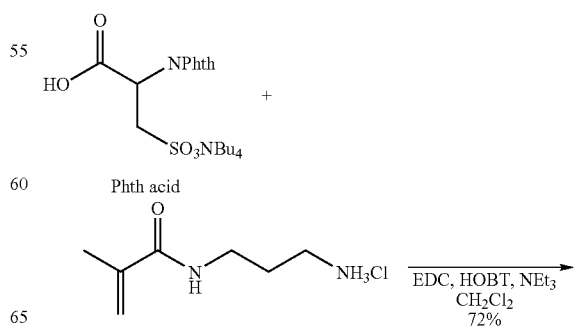

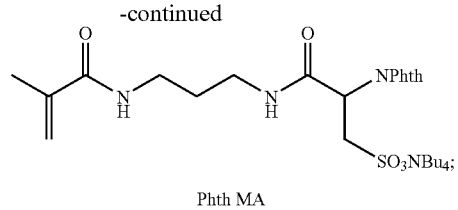

Phth MA d) AminoCysMA as follows:

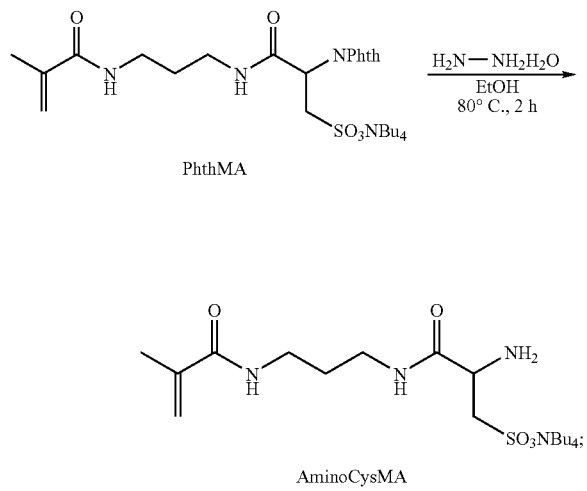

and e) HPTS-Cys-MA as follows:

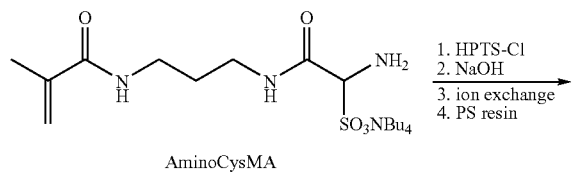

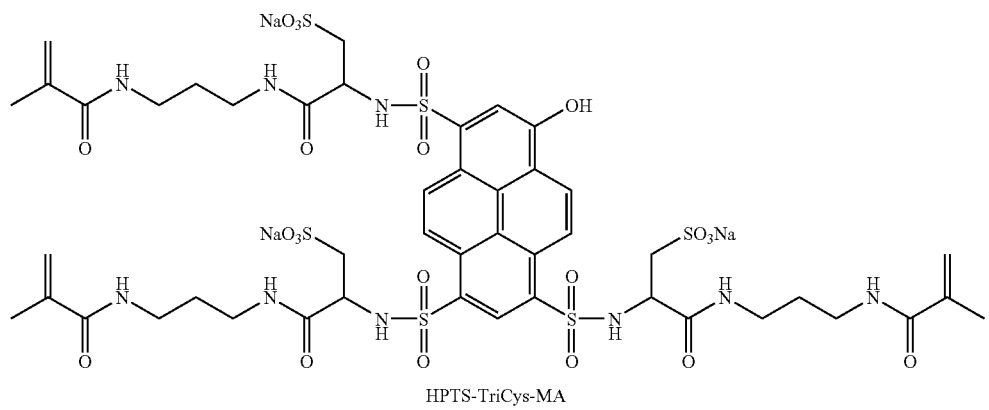

HPTS-TriCys-MA

DETAILED DESCRIPTION OF THE PREFERRED EMBODIMENT

Fluorescent Dyes

Figure 1:
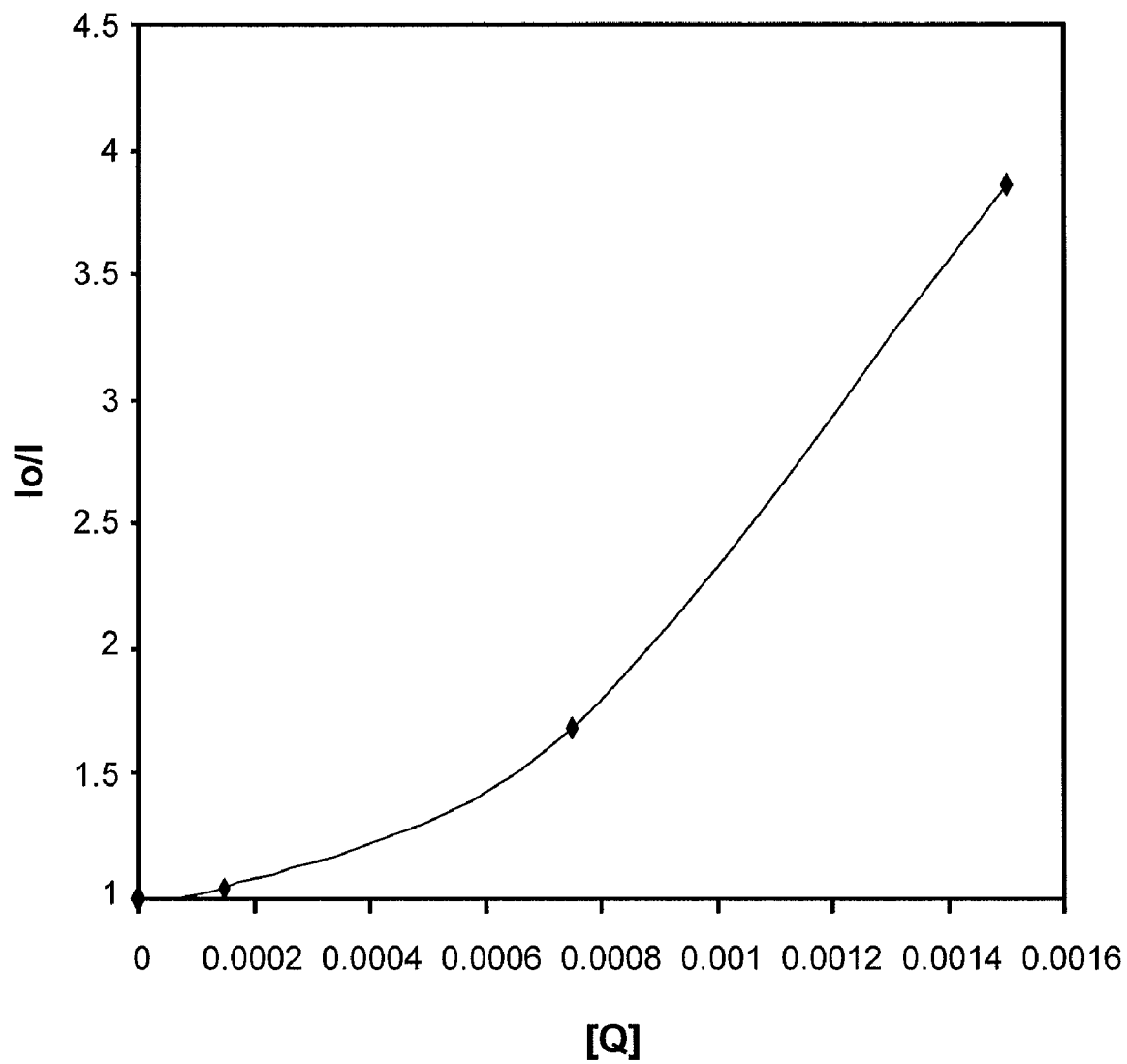
FIG. 1. Stern-Volmer Quenching of HPTS-CysMA/3,3'-oBBV in Solution. Shows the relative emission change (Stern-Volmer curve) upon addition of 3,3'-oBBV indicating the quenching of HPTS-CysMA with 3,3'-oBBV.

The fluorescent dyes of the invention are derivatives of 8-hydroxypyrene-1,3,6-trisulfonate (HPTS). The counterions can be $H^+$ or any other cation. HPTS exhibits two excitation wavelengths at around 405 nm and around 450 nm, which correspond to the absorption wavelengths of the acid and its conjugate base, respectively. The shift in excitation wavelength is due to the pH-dependent ionization of the hydroxyl group on HPTS. As the pH increases, HPTS shows an increase in absorbance at about 450 nm, and a decrease in absorbance below about 420 nm. The pH-dependent shift in the absorption maximum enables dual-excitation ratiometric detection in the physiological range. The dyes may be used with a quencher comprising boronic acid, such as 3,3'-oBBV.

A generic structure of dyes in accordance with preferred embodiments of the present invention is:

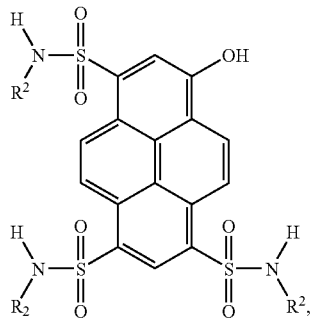

wherein:
$R^2$ is

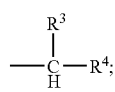

$R^3$ is $-(CH_2)_n-A^-M^+$, wherein n is 1-4, wherein $A^-$ is an anionic group selected from the group consisting of $SO_3^-$, $HPO_3^-$, $CO_2^-$ and

and wherein $M^+$ is a cationic group selected from the group consisting of $H^+$, an alkali metal ion, $Li^+$, $Na^+$, $K^+$, $Rb^+$, $Cs^+$, $Fr^+$, an onium ion and $NR_4^+$, wherein R is selected from the group consisting of alkyl, alkylaryl and aromatic groups);

$R^4$ is

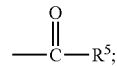

$R^5$ is selected from the group consisting of

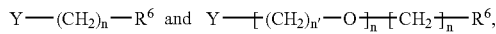

wherein n is equal to 1-10, n' is equal to 2-4 and Y is selected from the group consisting of NH and O;

$R^6$ is selected from the group consisting of $NHR^7$, $OR^7$ and $CO_2H$; and $R^7$ is H or an ethylenically unsaturated group selected from the group consisting of methacryloyl, acryloyl, styryl, acrylamide and methacrylamido.

Another generic structure of dyes in accordance with preferred embodiments of the present invention is:

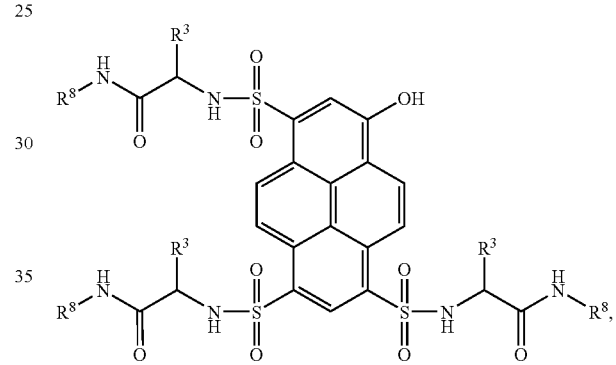

where:
$R^3$ is $-(CH_2)_n-A^-M^+$,
wherein n is 1-4,
wherein $A^-$ is an anionic group selected from the group consisting of $SO_3^-$, $HPO_3^-$, $CO_2^-$ and

and
wherein $M^+$ is a cationic group selected from the group consisting of $H^+$, an alkali metal ion, $Li^+$, $Na^+$, $K^+$, $Rb^+$, $Cs^+$, $Fr^+$, an onium ion and $NR_4^+$, wherein R is selected from the group consisting of alkyl, alkylaryl and aromatic groups);

$R^4$ is

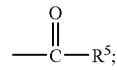

$R^8$ is selected from the group consisting of

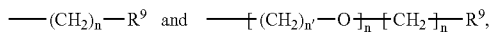

wherein n is equal to 1-10, n' is equal to 2-4;
$R^9$ is selected from the group consisting of $NHR^{10}$, $OR^{10}$ and $CO_2H$; and
$R^{10}$ is H or an ethylenically unsaturated group selected from the group consisting of methacryloyl, acryloyl, styryl, acrylamido and methacrylamido.

The structure of HPTS-Cys-MA is as follows:

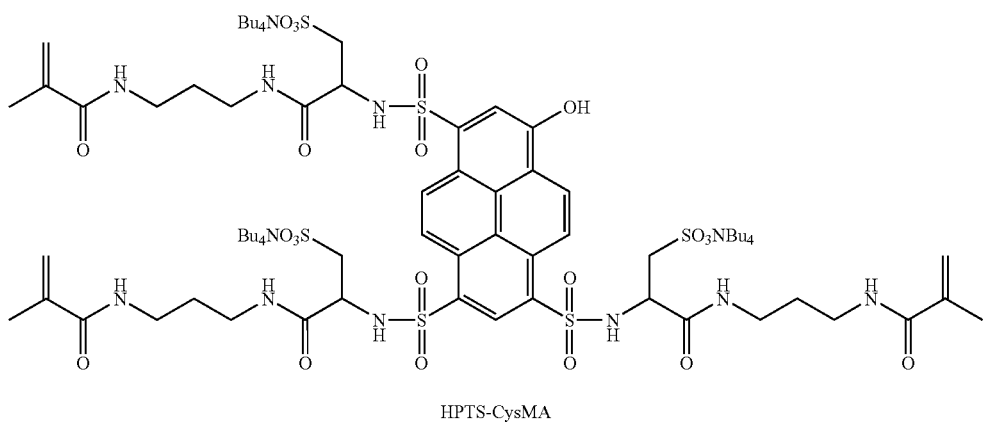

HPTS-CysMA

As indicated in the generic structures above, substitutions other than Cys-MA on the HPTS core are consistent with aspects of the present invention, as long as the substitutions are negatively charged and have a polymerizable group. For example, either L or D stereoisomers of cysteic acid may be used. In some embodiments, only one or two of the sulfonic acids may be substituted. Likewise, in variations to HPTS-CysMA shown above, other counterions besides $NBu_4^+$ may be used, including positively charged metals, e.g., $Na^+$. In other variations, the sulfonic acid groups may be replaced with e.g., phosphoric, carboxylic, etc. functional groups.

For comparison, the structure of HPTS-LysMA is pictured below as follows:

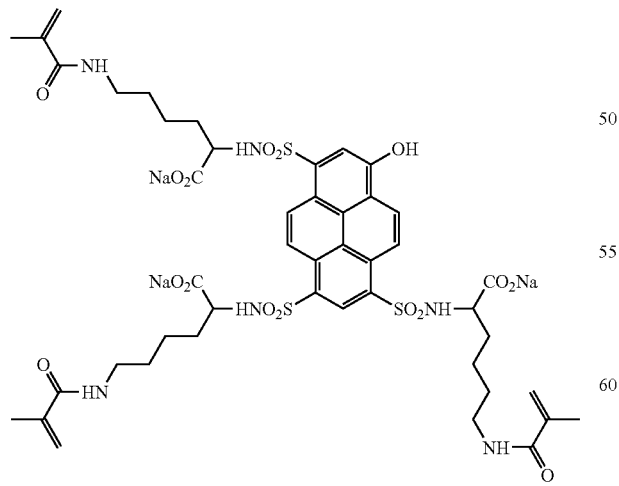

HPTS-LysMA

First Method of Making the Generic Class of Compounds to which HPTS-Cys-MA Belongs A first method of making the generic class of compounds to which HPTS-Cys-MA belongs is disclosed in accordance with another embodiment of the present invention. The method comprises the following steps:

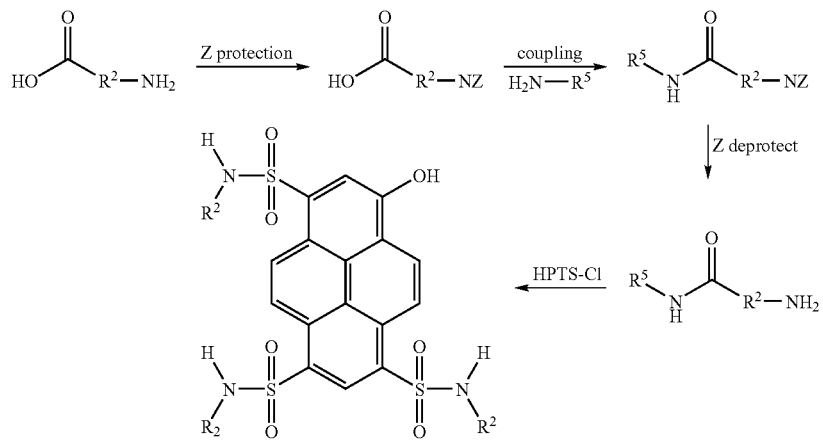

wherein:
$R^2$ is

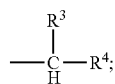

$R^3$ is —$(CH_2)_n$—$A^-M^+$,
  wherein n is 1-4,
  wherein $A^-$ is an anionic group selected from the group consisting of $SO_3^-$, $HPO_3^-$, $CO_2^-$ and

and
  wherein $M^+$ is a cationic group selected from the group consisting of $H^+$, an alkali metal ion, $Li^+$, $Na^+$, $K^+$, $Rb^+$, $Cs^+$, $Fr^+$, an onium ion and $NR_4^+$, wherein R is selected from the group consisting of alkyl, alkylaryl and aromatic groups);

$R^4$ is

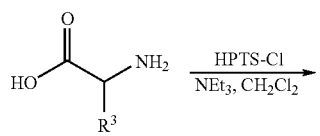

$R^5$ is selected from the group consisting of $Y$—$(CH_2)_n$—$R^6$ and $Y$—$[(CH_2)_{n'}$—$O]_n$—$[CH_2]_n$—$R^6$ wherein n is equal to 1-10, n' is equal to 2-4 and Y is selected from the group consisting of NH and O;

$R^6$ is selected from the group consisting of $NHR^7$, $OR^7$ and $CO_2H$;

$R^7$ is H or an ethylenically unsaturated group selected from the group consisting of methacryloyl, acryloyl, styryl, acrylamide and methacrylamido; and Z is an amino protecting group selected from the group consisting of phthalimido, Boc and Fmoc).

Second Method of Making the Generic Class of Compounds to which HPTS-Cys-MA Belongs A second method of making the generic class of compounds to which HPTS-Cys-MA belongs is disclosed in accordance with another embodiment of the present invention. The method comprises the steps of:

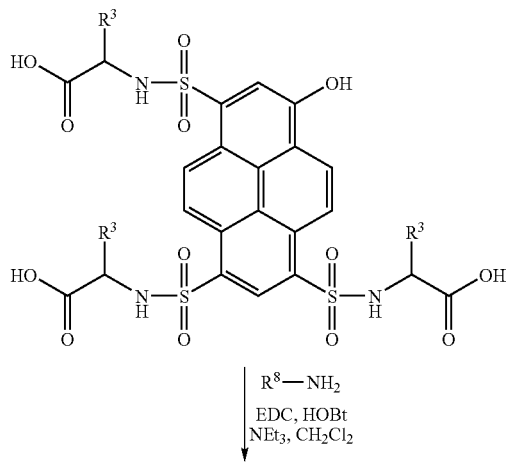

-continued

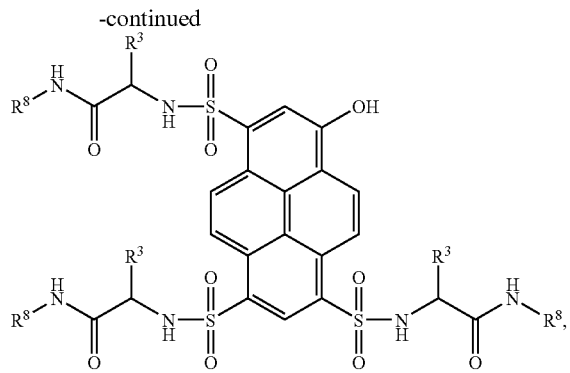

wherein:
$R^3$ is $-(CH_2)_n-A^-M^+$,
 wherein n is 1-4,
 wherein $A^-$ is an anionic group selected from the group consisting of $SO_3^-$, $HPO_3^-$, $CO_2^-$ and

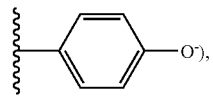

and
 wherein $M^+$ is a cationic group selected from the group consisting of $H^+$, an alkali metal ion, $Li^+$, $Na^+$, $K^+$, $Rb^+$, $Cs^+$, $Fr^+$, an onium ion and $NR_4^+$, wherein R is selected from the group consisting of alkyl, alkylaryl and aromatic groups);
$R^8$ is selected from the group consisting of

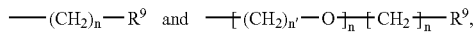

wherein n is equal to 1-10, n' is equal to 2-4;

$R^9$ is selected from the group consisting of $NHR^{10}$, $OR^{10}$ and $CO_2H$; and $R^{10}$ is H or an ethylenically unsaturated group selected from the group consisting of methacryloyl, acryloyl, styryl, acrylamide and methacrylamido.

First Specific Method of Synthesizing HPTS-Cys-MA

Cysteic acid 1 (0.5 mmols, 94 mg-L stereoisomer was used in this synthesis; however, D stereoisomer may also be used) was treated with an aqueous solution of tetrabutylammonium hydroxide (0.5 mmols, 4 mL of 0.125 M solution) at room temperature (scheme 1). After stirring for 30 min, the solution was lyophilized to give 2 and the residue was dissolved in dichloromethane (2 mL). Triethylamine (0.6 mmols, 61 mg) was added followed by the dropwise addition of HPTS-Cl (0.1 mmols, 52 mg) in dichloromethane (2 mL). The mixture stirred for 18 h at room temperature and was then concentrated in vacuo. The residue was dissolved in hot isopropyl alcohol and loaded onto a Biotage SP125M silica gel cartridge and eluted with $NH_4OH$:isopropyl alcohol (1:3) to give HPTS-CysOH as a yellow powder (0.024 mmols, 39 mg, 24%). $^1H$ NMR ($D_2O$, 500 MHz) δ 0.85 (t, J=7.4 Hz, 36H), 1.20 (s, J=7.4 Hz, 24H) 1.44 (m, 24H), 2.94 (m, 24H), 3.24 (m, 6H), 4.31 (m, 3H), 8.19 (d, J=16.8 Hz, 2H), 8.36 (d, J=9.0 Hz, 1H), 8.50 (d, J=9.3 Hz, 1H), 8.64 (d, J=9.3 Hz, 1H), 8.71 (d, J=7.1 Hz, 1H), 8.90 (m, 4H), 9.19 (d, J=12.0 Hz, 2H).

Scheme 1

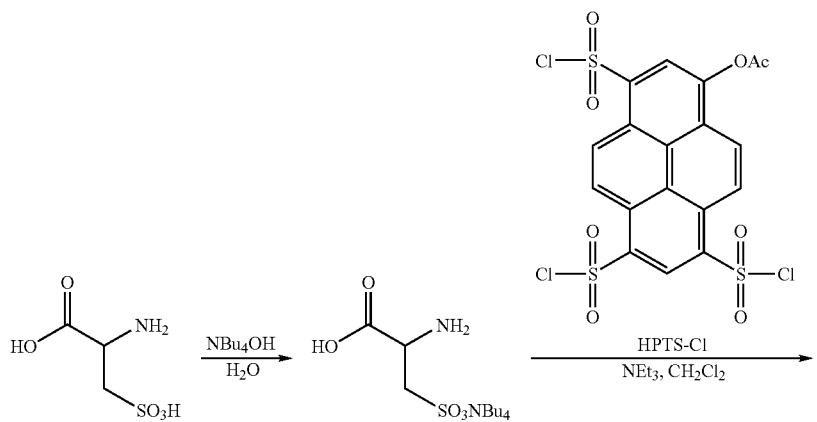

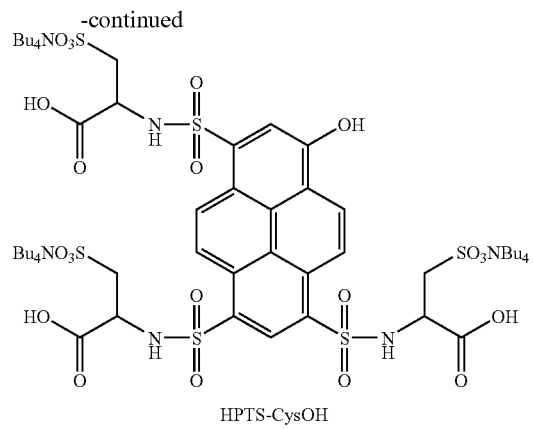

HPTS-CysOH

To a solution of HPTS-CysOH (0.0183 mmols, 30 mg) in DMF (1 mL) was added N-ethyl-N'-(3-dimethylaminopropyl)carbodiimide hydrochloride (EDC) (0.055 mmols 10.5 mg), 1-hydroxybenzotriazole (HOBT) (0.055 mmols, 7.4 mg), N,N,N',N'-tetramethyl-O-(1H-benzotriazol-1-yl)uronium hexafluorophosphate (HBTU) (0.055 mmols, 21 mg), and N,N'-diisopropylethylamine (DIEA) (0.183 mmols, 24 mg). After the solution was stirred at room temperature for 20 min, N-(3-aminopropyl)methacrylamide hydrochloride was added and the mixture was stirred for 48 h. The reaction mixture was precipitated with acetone:ether (5:1, 10 mL) to give an oily residue. The residue was triturated with acetone (10 mL) and sonicated for 30 min to give HPTS-CysMA as a crude mixture (35 mg of orange powder).

Scheme 2

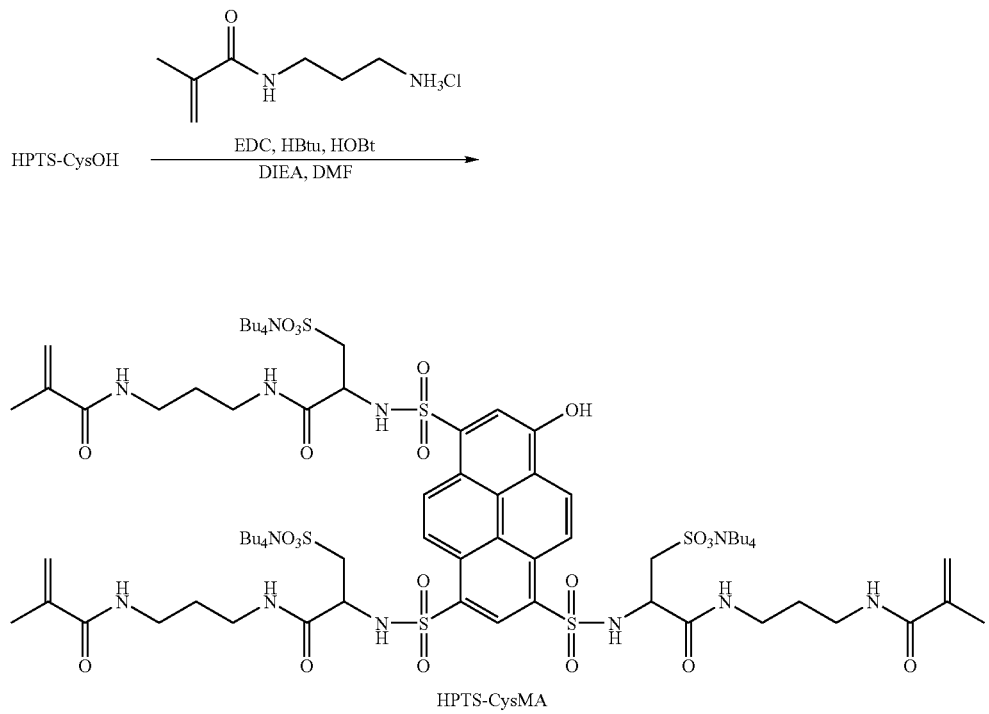

HPTS-CysMA

Second Specific Method of Synthesizing HPTS-Cys-MA

Step 1: Synthesis of TBCys:

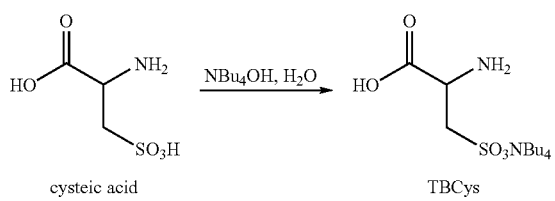

cysteic acid → TBCys

In a 500-mL beaker equipped with a magnetic stirring bar, (L)-Cysteic acid (129.24 mmols, 24.1913 g) was dissolved in H$_2$O (100 mL) and treated with tetrabutylammonium hydroxide (129.24 mmols, 129.24 mL, 128.59 g of a 1.0 M aqueous solution). The mixture was stirred at room temp for 30 min and then frozen using a low temperature (dry ice/2-propanol) bath. The solid was lyophilized over three days to give a glassy material that was re-dissolved in CH$_2$Cl$_2$ (300 mL). The solution was evaporated to dryness in a 500-mL flask to give TBCys as a white foam. Yield: 53.3756 g, 129 mmols, 100%.

Step 2: Synthesis of Phth acid:

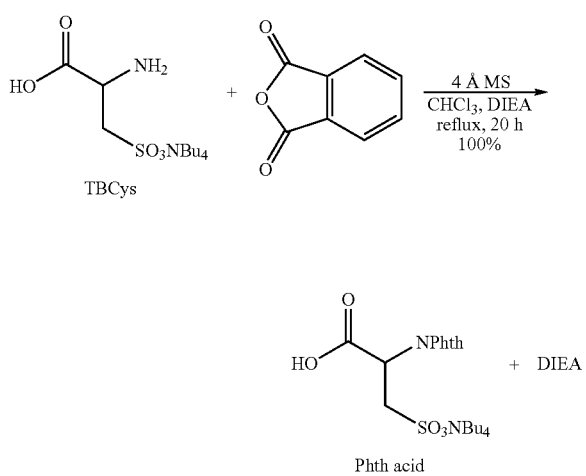

TBCys

Phth acid

In a 500-mL flask equipped with a magnetic stirring bar, TBCys (129 mmols, 53.1936 g) was dissolved in CHCl$_3$ (129 mL), and N,N'-diisopropylethyl amine (65 mmols, 8.385 g, 11.3 mL) was added followed by phthalic anhydride (129 mmols, 19.10748 g) and 4-angstrom molecular sieves (50 mL); the mixture was refluxed for 48 h. The mixture was filtered through a 600-mL glass fritted funnel and the filtrate was concentrated in vacuo and washed with diethyl ether (2×100 mL) and dried under reduced pressure to give Phth acid complexed with N,N'-diisopropylethyl amine. Yield: 70 g, 129 mmols, 100%. $^1$H NMR (CDCl$_3$, 500 MHz) δ 0.95 (t, J=7.4 Hz, 12H), 1.30 (m, 8H), 1.38 (q, J=7.4 Hz, 8H), 1.61 (m, 8 H), 2.96 (q, J=7.4 Hz, 1H), 3.23 (m, 8H), 3.55 (sept, J=6.7, 1H), 3.62 (m, 1H), 3.86 (dd, J$_1$=5 Hz, J$_2$=9.4 Hz, 1H), 5.31 (dd, J$_1$=5.4 Hz, J$_2$=1.2 Hz, 1H), 7.65 (q, J=3 Hz, 2H), 7.55 (q, J=3 Hz, 2H); $^{13}$C NMR (CDCl$_3$, 125 MHz) δ 12.0, 13.8, 18.1, 19.8, 24.0, 41.7, 50.4, 51.0, 53.1, 58.7, 123.0, 132.8, 133.52, 167.9, 170.7; HPLC supelcosil LC-8-DB, 5 μm, 150 mm×4.6 mm, λ=254 nm, gradient elution (30 to 70% MeOH) with MeOH/TBAP, R$_f$=5.9 min.

Step 3: Synthesis of Phth MA:

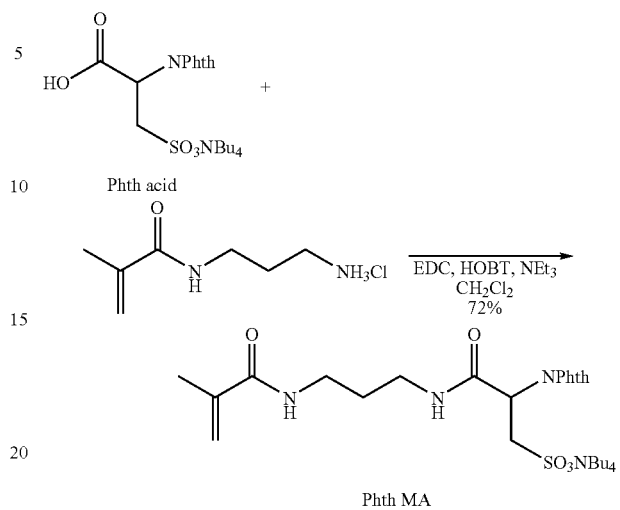

Phth acid

Phth MA

In a 250-mL round bottom flask equipped with a magnetic stirring bar, Phth acid (24.9 mmols, 13.46 g) was dissolved in CH$_2$Cl$_2$ (85 mL) at 0° C. and EDC (27 mmols, 5.157 g), HOBT (27 mmols, 3.645 g), and triethylamine (54 mmols, 5.4 g, 7.5 mL) were added sequentially; the mixture was stirred under nitrogen for 20 min. N-(3-Aminopropyl)methacrylamide hydrochloride (27 mmols, 4.806 g) was added and the mixture was allowed to reach room temperature over 2 h and then was stirred for an additional 14 h at room temp. The solution was treated with sat. NaHCO$_3$ (100 mL) and extracted with CH$_2$Cl$_2$ (3×20 mL). The CH$_2$Cl$_2$ layer was dried over MgSO$_4$ and concentrated in vacuo to give an orange oil that was loaded onto a Biotage KP-sil 40M cartridge. The material was purified via gradient elution with 5 to 15% MeOH/CH$_2$Cl$_2$. The product was isolated as a white foam, yield 72%. $^1$H NMR (CDCl$_3$, 500 MHz) δ 0.99 (t, J=7.4 Hz, 12H), 1.44 (sext, J=7.4 Hz, 8H), 1.66 (m, 10H), 1.89 (s, 3H), 3.28 (m, 11H), 3.38 (sext, 2H), 3.96 (dd, J$_1$=9 Hz, J$_2$=5.9 Hz, 1H), 5.22 (t, J=1.4 Hz, 1H), 5.44 (dd, J$_1$=1.9 Hz, J$_2$=9.0 Hz, 1H), 5.69 (s, 1H), 5.91 (t, J=6.0 Hz, 1H), 7.70 (m, 2H), 7.82 (m, 2H), 9.09 (t, j=5.8 Hz, 1H); $^{13}$C NMR (CDCl$_3$, 125 MHz) δ 13.8, 18.7, 19.8, 24.1, 29.1, 36.0, 36.4, 50.5, 53.2, 58.9, 119.6, 123.4, 132.3, 134.0, 140.0, 167.9, 168.5, 169.3; HPLC supelcosil LC-8-DB, 5 μm, 150 mm×4.6 mm, λ=254 nm, gradient elution (30 to 70% MeOH) with MeOH/TBAP, R$_f$=6.6 min.

Step 4: Synthesis of AminoCysMA:

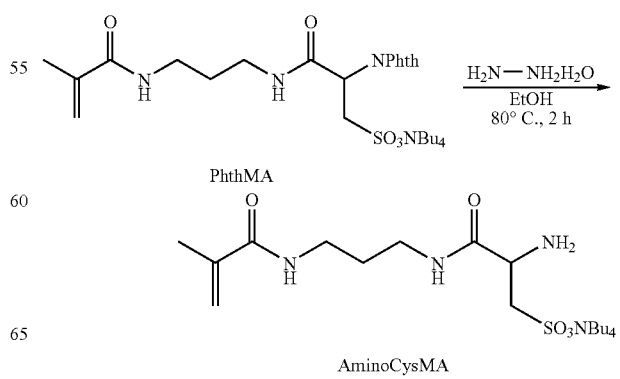

PhthMA

AminoCysMA

In a 100-mL round bottom flask equipped with a magnetic stirring bar, PhthMA (2.59 mmols, 1.7225 g) was dissolved in ethanol (20 mL) and hydrazine monohydrate (2.59 mmols, 0.130 g, 0.126 mL) was added and the mixture was heated at 80° C. for two hours. The solution was cooled to room temperature and $CH_2Cl_2$ (20 mL) was added. The precipitate that was formed was filtered using a fritted funnel and washed with additional $CH_2Cl_2$ (10 mL) and the filtrate was concentrated in vacuo. The residue was dissolved in $CH_2Cl_2$ (5 mL) and loaded onto a Biotage KP-NH 40M cartridge and eluted with 1% to 15% $MeOH/CH_2Cl_2$. The fractions were collected and concentrated in vacuo to give aminoCysMA as a colorless oil. Yield: 60%. $^1H$ NMR ($CD_3OD$, 500 MHz) δ 1.03 (t, J=7.4 Hz, 12H), 1.42 (sext, J=7.4 Hz, 8H), 1.66 (m, 8H), 1.95 (s, 3H), 2.87 (q, $J_1$=9.4 Hz, $J_2$=4.4 Hz, 1H), 3.23 (m, 10H), 3.81 (dd, $J_1$=3.3 Hz, $J_2$=6.0 Hz, 1H), 5.37 (s, 1H), 5.73 (s, 1H); HPLC supelcosil LC-8-DB, 5 μm, 150 mm×4.6 mm, λ=254 nm, gradient elution (30 to 70% MeOH) with MeOH/TBAP, $R_t$=3.5 min.

Step 5: Synthesis of HPTS-Cys-MA:

solid. Additional product was isolated from the washings using the same MeOH-extraction procedure. Yield: 40%. $^1H$-NMR (500 MHz, D2O, ppm): 1.18-1.09 (m, 6H), 1.76-1.53 (m, 9H), 2.73-2.23 (m, 12H); HPLC supelcosil LC-8-DB, 5 μm, 150 mm×4.6 mm, FLD detector, gradient elution (30 to 70% MeOH) with MeOH/TBAP, $R_t$=11.6 min; MALDI-TOF for $C_{46}H_{58}N_9Na_3O_{22}S_6$ [MH]$^+$: 1350, [MH-Na+H]$^+$:1328, [MH-2Na+2H]$^+$: 1306, [MH-3Na+3H]$^+$: 1284 (major).

Quenchers

As used herein, the term "quencher" refers to a compound that reduces the emission of a fluorescent dye, e.g., HPTS-Cys-MA, when in its presence.

In some embodiments, a quencher moiety provides glucose recognition. Such moieties preferably comprise an aromatic boronic acid. More specifically, the boronic acid is covalently bonded to a conjugated nitrogen-containing heterocyclic aromatic bis-onium structure (e.g., a viologen) in which the boronic acid reacts reversibly or irreversibly with glucose in

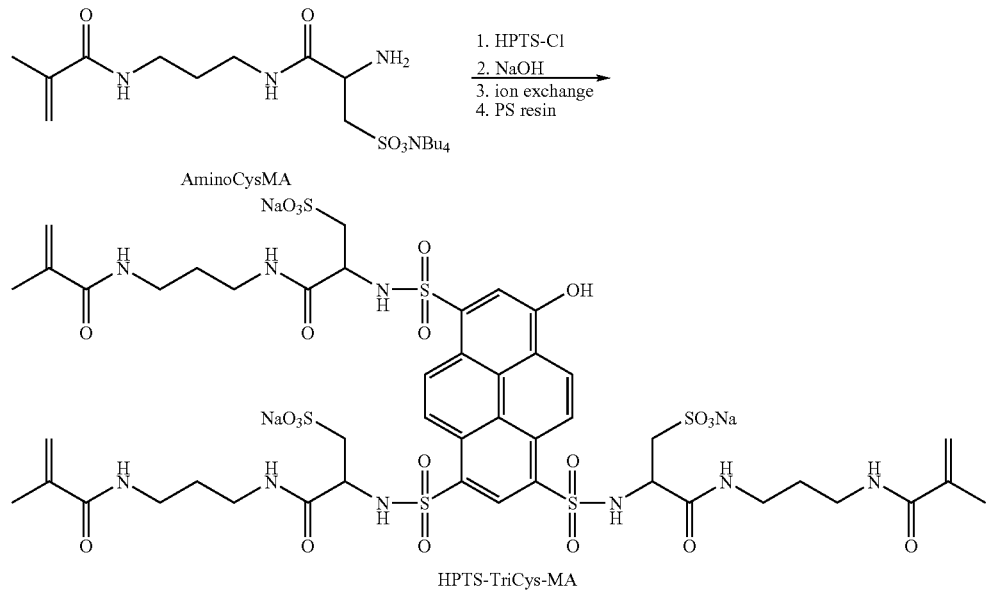

In a 50-mL round bottom flask, AminoCysMA (1.09 mmols, 0.5827 g) was dissolved in $CH_2Cl_2$ (10 mL) and HPTS-Cl (0.29 mmols, 0.163 g) was added. Triethylamine (1.1 mmols, 0.153 mL) was added and the mixture was stirred at room temperature for 16 h. The red solution was treated with 1 M NaOH (10 mL), stirred for 30 min., and the two layers were separated in a separatory funnel. The orange-aqueous layer was passed through a column of Dowex 50W resin (in the H$^+$ form) to give a yellow/green solution with a pH=4 as determined by pH paper. The aqueous solution was then passed through a column of Dowex 50W (in the Na$^+$ form) to obtain the crude sodium salt of HPTS-CysMA. The solution was adsorbed onto polystyrene-divinylbenzene resin (250 g) and washed with $H_2O$ (5×500 mL). The washings were kept and the adsorbed material was removed from the resin with MeOH (1 L). The MeOH/water extract was evaporated to dryness after multiple co-evaporations with fresh MeOH (4×500 mL) and the residue was re-dissolved in MeOH (0.5 mL). Acetone (15 mL) was added and the precipitate was collected by centrifugation and dried under a stream of argon to give HPTS-Cys-MA as an orange/yellow aqueous, organic or combination media to form boronate esters. The extent of the reaction is related to glucose concentration in the medium.

Bis-onium salts are prepared from conjugated heterocyclic aromatic dinitrogen compounds. The conjugated heterocyclic aromatic dinitrogen are, e.g., dipyridyls, dipyridyl ethylenes, dipyridyl phenylenes, phenanthrolines, and diazafluorenes. It is understood that all isomers of said conjugated heterocyclic aromatic dinitrogen compounds in which both nitrogens can be substituted are useful in this invention. Boronic acid-substituted viologens and boronic acid-substituted polyviologens are described in detail in co-pending U.S. application Ser. No. 11/671,880; incorporated herein in its entirety by reference thereto.

In other embodiments, pyridinium boronic acid quenchers are used in combination with the dyes of the present invention. Pyridinium boronic acid quenchers are described in detail in U.S. Provisional Application No. 60/915,372; incorporated herein in its entirety by reference thereto.

In one preferred embodiment, 3,3'-oBBV may be used as a quencher moiety. The structure of 3,3'-oBBV is:

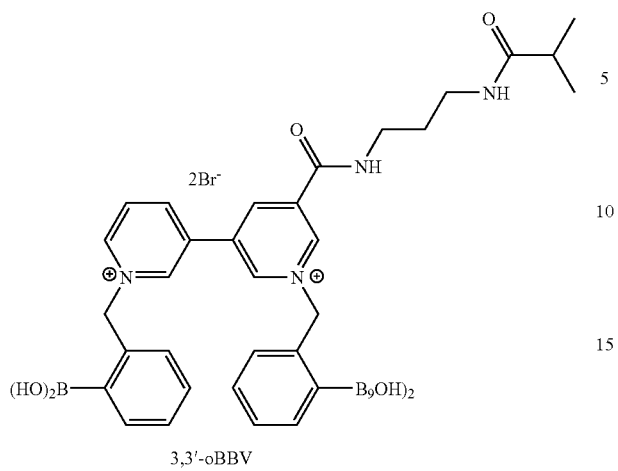

3,3'-oBBV

Functional Analysis of Dyes

HPTS-Cys-MA was tested in solution using the fluorimeter to determine how it compares with HPTS-LysMA. Stern-Volmer and glucose response studies were carried out back to back under identical conditions to ensure direct comparison.

Solution Studies

To a solution of HPTS-CysMA ($1 \times 10^{-5}$ M in pH 7.4 PBS) was added increasing amounts of 3,3'-oBBV (30 mM in MeOH) and the fluorescence emission measured after each addition. FIG. 1 gives the relative emission change (Stern-Volmer curve) upon addition of 3,3'-oBBV indicating the quenching of HPTS-CysMA with 3,3'-oBBV. The fluorimeter settings were as follows: 1% attenuation, ex slit 8 nm, em slit 12 nm, 486 nm ex λ, 537 nm em λ.

Figure 2:
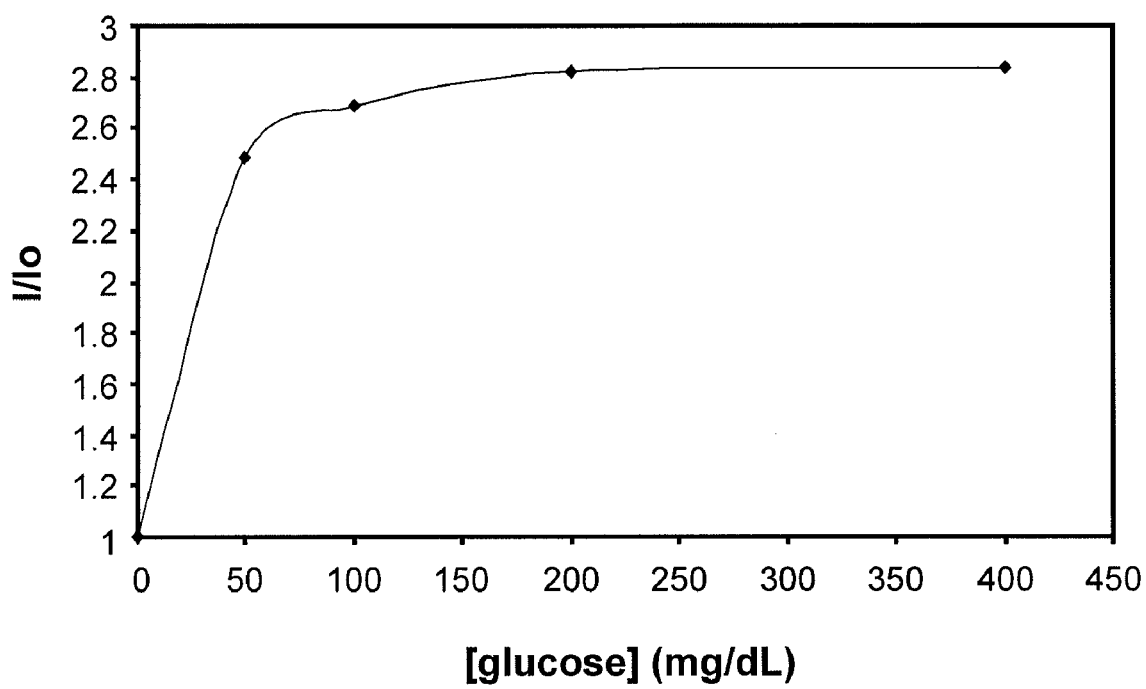
FIG. 2. Glucose Response of HPTS-CysMA/3,3'-oBBV in Solution. Shows the fluorescence emission measured after addition of glucose to HPTS-CysMA and 3,3'-oBBV.

HPTS-CysMA ($1 \times 10^{-5}$ M) and 3,3'-oBBV ($3 \times 10^{-3}$ M) were titrated with a stock solution of glucose (31250 mg/dL) in pH 7.4 PBS and the fluorescence emission measured after each addition of glucose The relative change upon addition of glucose is given in FIG. 2.

Polymer Studies

Figure 3:
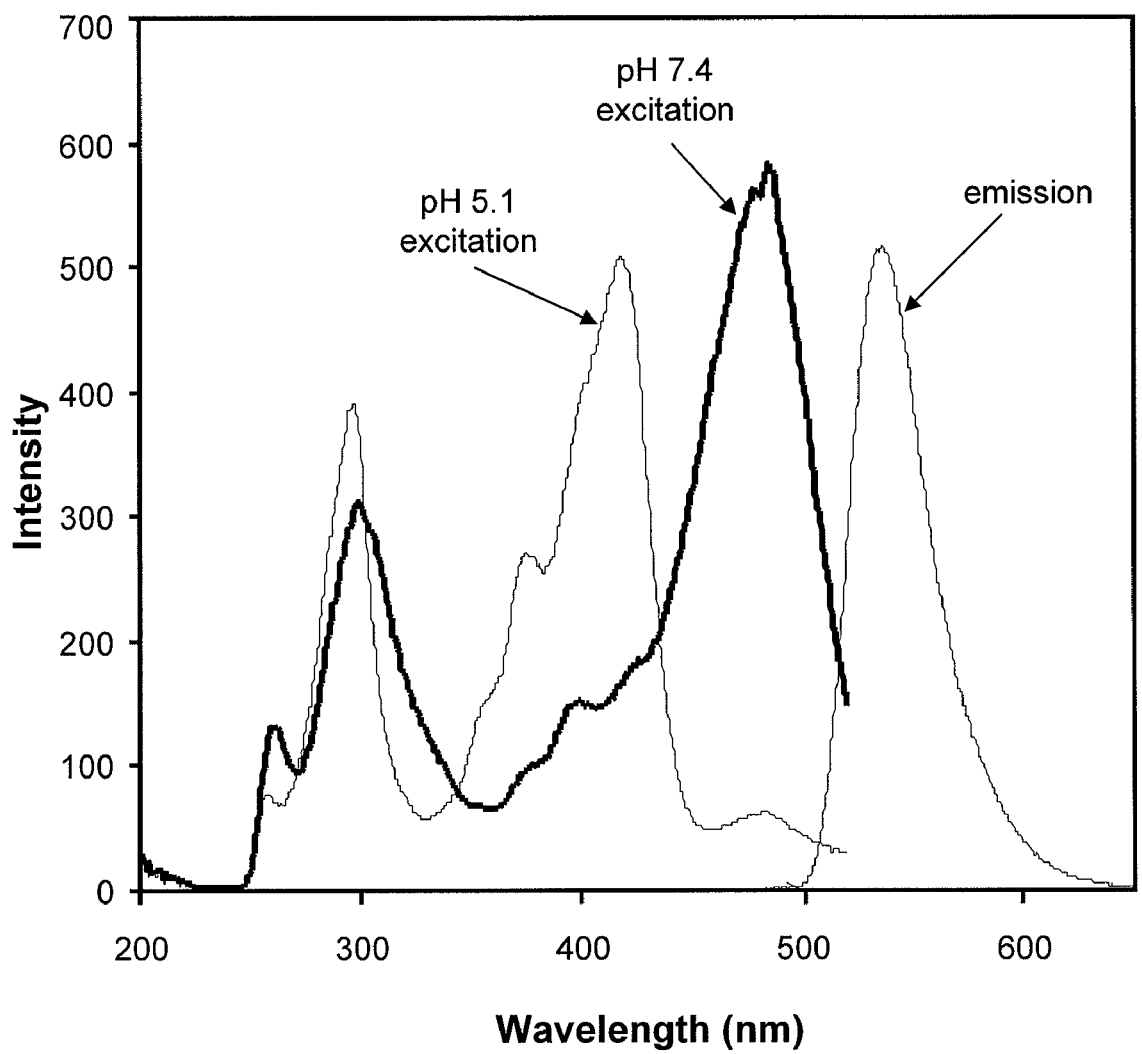
FIG. 3. Fluorescence Spectra of HPTS-CysMA in Hydrogel. Shows fluorescence excitation and emission spectra of a polymer hydrogel comprising HPTS-CysMA.

HPTS-CysMA (1 mg), N,N'-dimethylacrylamide (400 mg), N,N'-methylenebisacrylamide (8 mg), HCl (10 μL of 1 M solution), and VA-044 (1 mg) were dissolved in water and diluted to 1 mL in a volumetric flask. The solution was freeze-pump-thawed (3×), injected into a mold containing a 0.005" polyimide spacer and polymerized at 55° C. for 16 h. The resultant film was placed in pH 7.4 phosphate buffer and its fluorescence excitation and emission spectra obtained (FIG. 3).

Figure 4:
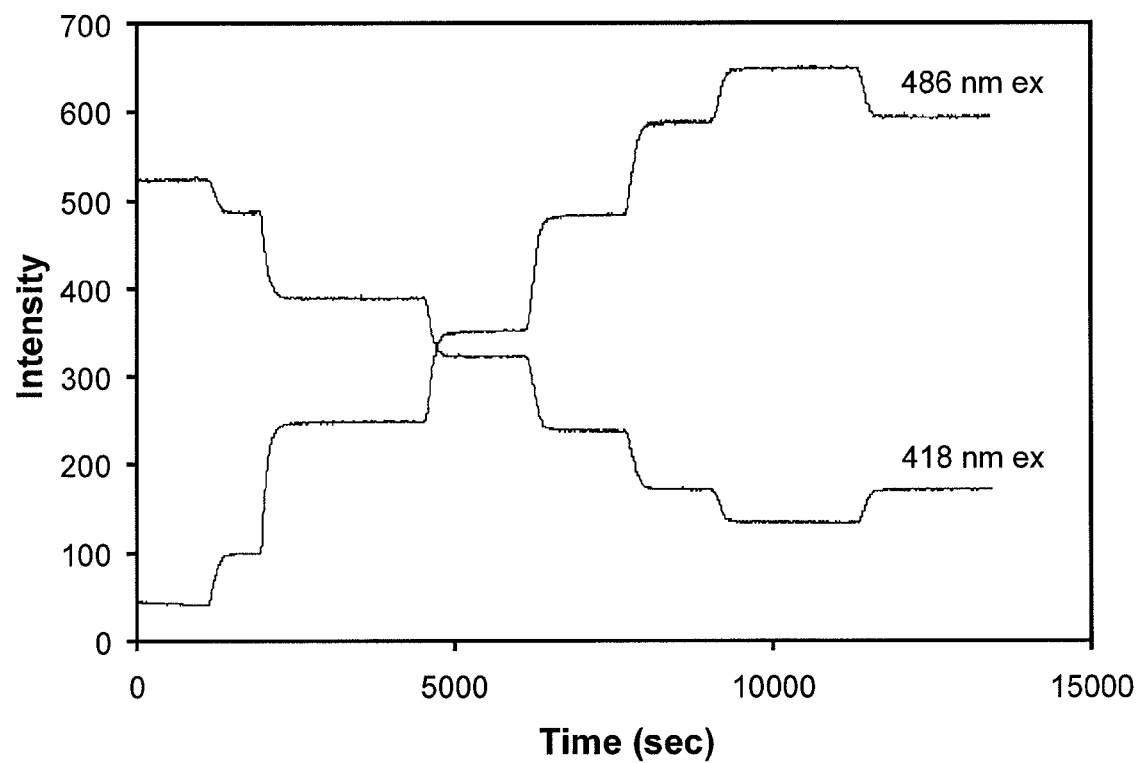
FIG. 4. Time Drive of HPTS-Cys-MA in hydrogel at Different pHs, Em=532 nm. Shows time drive of HPTS-CysMA in hydrogel at different pH's.
Figure 5:
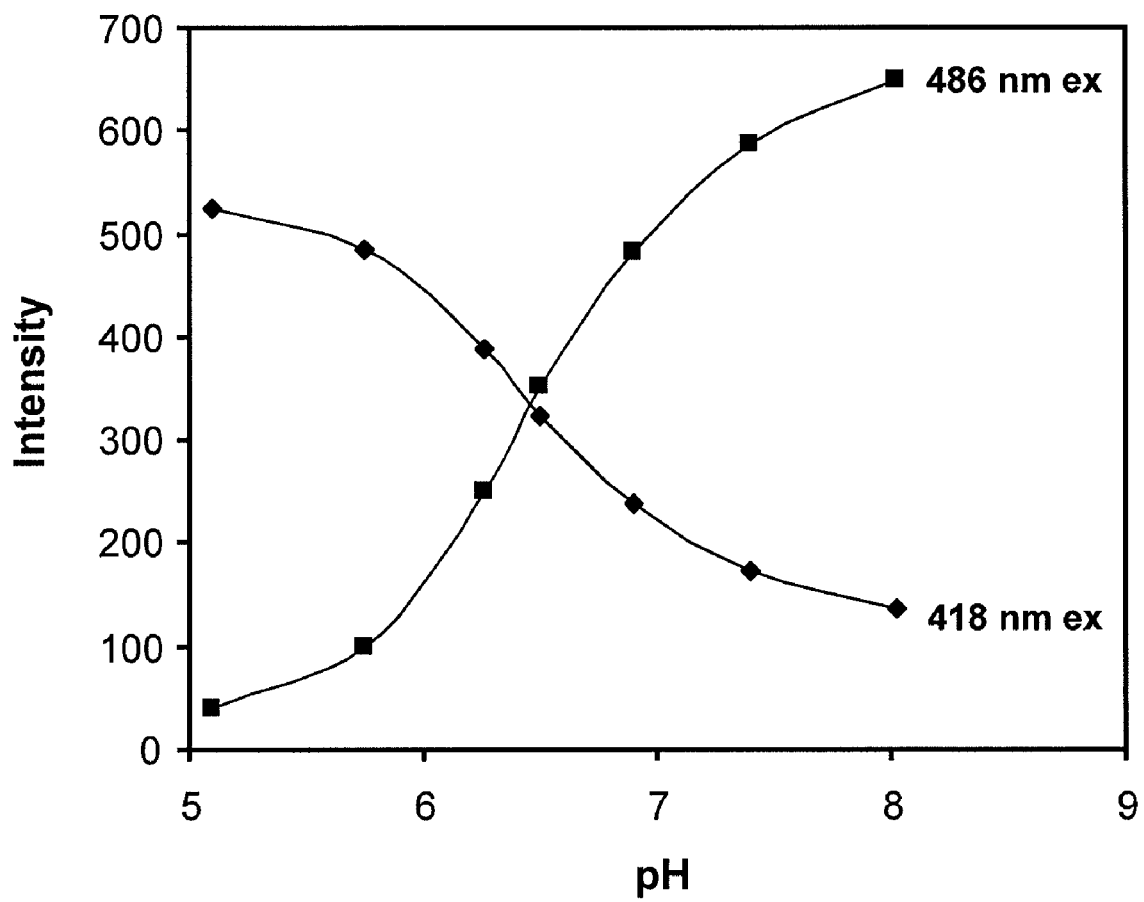
FIG. 5. pH profile of HPTS-Cys-MA at two different excitations, Em=532 nm. Shows pH profile of HPTS-CysMA at two different excitation wavelengths.

The film was tested in a flow cell configuration at various pHs (initially at pH 5.1; changed to pH 5.75, 6.26, 6.5, 6.9, 7.4, 8.02, and then back to pH 7.4) at two different excitation wavelengths (418 nm and 486 nm) and was monitored at one emission wavelength (532 nm) over time (FIG. 4). The fluorimeter settings were as follows: ex slit 5 nm, em slit 3.5 nm, 515 nm cutoff filter, 418 nm ex λ, 486 nm ex λ, 532 nm em λ. The pH profile is summarized in FIG. 5.

Figure 6:
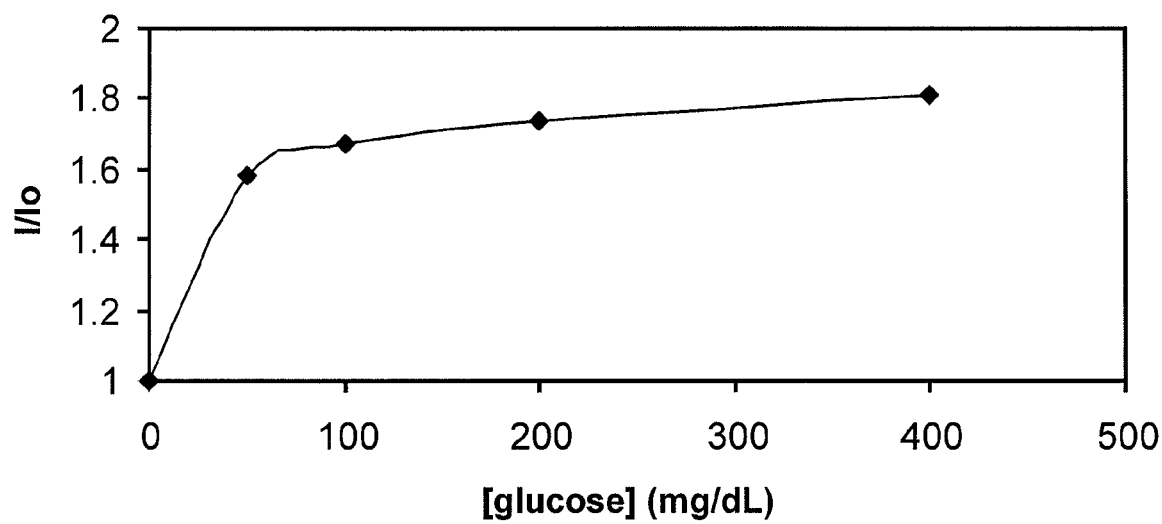
FIG. 6. Glucose Response of HPTS-CysMA/3,3'-oBBV in hydrogel. Shows the glucose response of HPTS-CysMA/3,3'-oBBV in a hydrogel.

HPTS-CysMA (2 mg), 3,3'-oBBV (15 mg), N,N'-dimethylacrylamide (400 mg), N,N'-methylenebisacrylamide (8 mg), HCl (10 μL of 1 M solution), and VA-044 (1 mg) were dissolved in water and diluted to 1 mL in a volumetric flask. The solution was freeze-pump-thawed (3×), injected into a mold containing a 0.005" polyimide spacer and polymerized at 55° C. for 16 h. The resultant film was placed in pH 7.4 phosphate buffer and was tested in a flow cell configuration with increasing amounts of glucose (0, 50, 100, 200, 400 mg/dL). The relative fluorescence change upon addition of glucose is given in FIG. 6. The fluorimeter settings were as follows: ex slit 8 nm, em slit 3.5 nm, 515 nm cutoff filter, 486 nm ex λ, 532 nm em λ.

Comparison Studies

Figure 7:
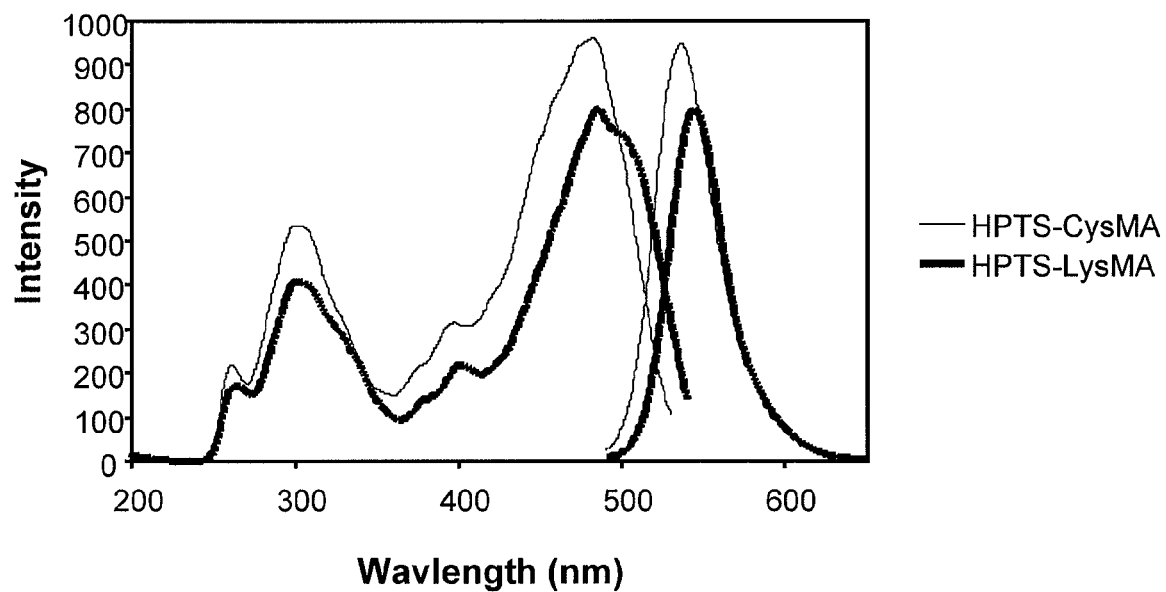
FIG. 7 Fluorescence Spectra of HPTS-CysMA and HPTS-LysMA. Shows a comparison of the fluorescence spectra of HPTS-Cys-MA and HPTS-Lys-MA. ($1\times10^{-5}$ M); Ex Slit 8 nm, Em Slit 12 nm.

A comparison of the fluorescence spectra of the CysMA and LysMA dyes in solution is shown in FIG. 7. The CysMA dye is blue-shifted relative to the LysMA dye.

Figure 8:
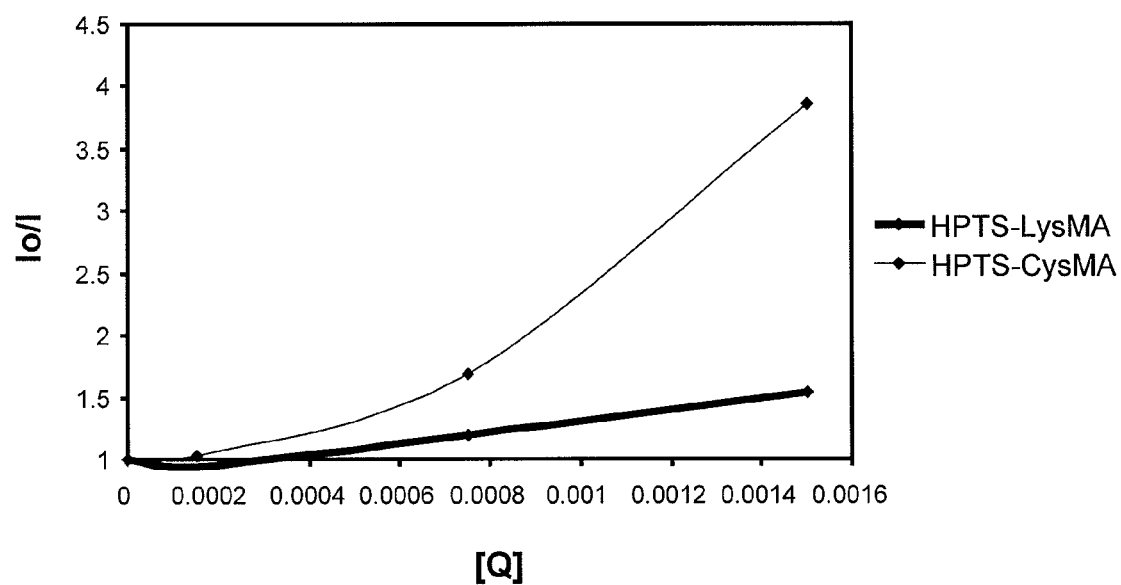
FIG. 8 Comparison of Stern-Volmer Quenching Using HPTS-LysMA and HPTS-CysMA with 3,3'-oBBV, [Dye]= $1\times10^{-5}$ M. Shows a comparison of 3,3'-oBBV Stern-Volmer quenching study using HPTS-Cys-MA and HPTS-Lys-MA.
Figure 9:
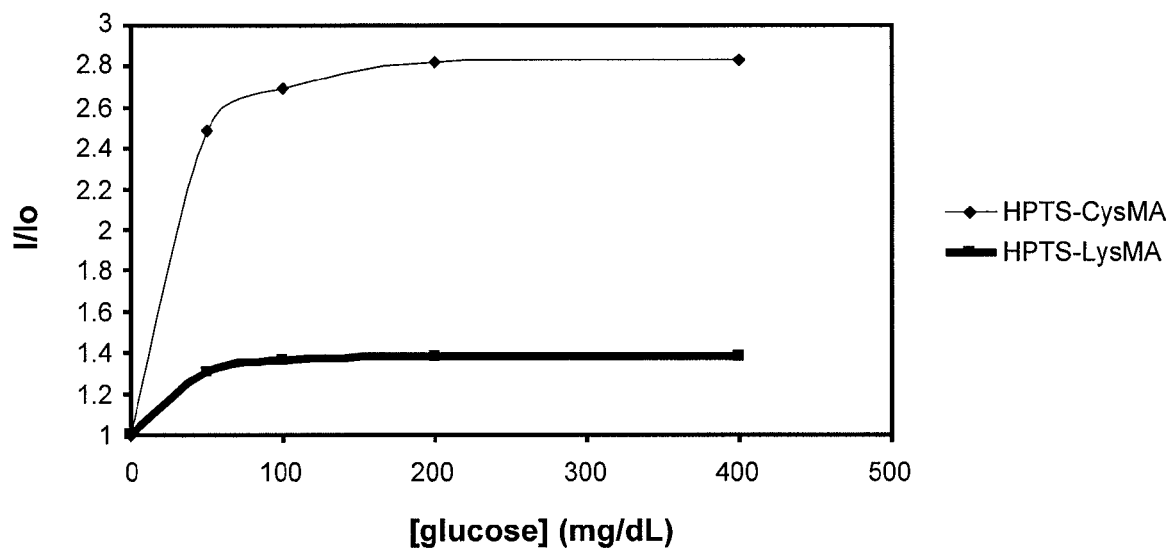
FIG. 9 Comparison of Glucose Modulation Using HPTS-LysMA and HPTS-CysMA with 3,3'-oBBV; [Dye]=$1\times10^{-5}$ M; Q/D=150. Shows a comparison glucose modulation using HPTS-Cys-MA and HPTS-Lys-MA with 3,3'-oBBV.

A comparison of the Stem-Volmer quenching study for CysMA and LysMA in solution is given in FIG. 8 and the glucose response is given in FIG. 9.

HPTS-CysMA is quenched more effectively with 3,3'-oBBV than is HPTS-LysMA. HPTS-CysMA forms a stronger complex because of the sulfonic acids than does HPTS-LysMA, which has carboxylic acids; the tighter complex leads to a greater glucose response. For this reason, dyes substituted with sulfonate groups are preferred.

Glucose Sensors

In one preferred embodiment, a device is disclosed for determining blood glucose concentration. The device comprises a sensor comprising an optical fiber sized for deployment intravascularly. The sensor further comprises a water-insoluble polymer matrix, wherein the polymer matrix is permeable to glucose; a fluorescent dye, as disclosed herein, associated with the polymer matrix; a quencher as disclosed herein, adapted to reversibly bind an amount of glucose related to the blood glucose concentration, wherein the quencher is also associated with the polymer matrix and operably coupled to the fluorescent dye, and wherein the quencher is configured to modulate the light emitted by the fluorescent dye related to the amount of bound glucose; at least one excitation light source; and an emission light detector.

A method is also disclosed for determining blood glucose concentration. The method comprises the steps of: providing the device described above; inserting the sensor into a blood vessel; irradiating the sensor at an excitation wavelength; detecting a fluorescence emission of the sensor at an emission wavelength; and determining the blood glucose concentration.

In some embodiments, for use in vitro not involving a moving stream, the sensing components are used as individual (discrete) components. The dye and quencher are mixed together in liquid solution, analyte is added, the change in fluorescence intensity is measured, and the components are discarded. Polymeric matrices that can be used to trap the sensing components to prevent leaching need not be present. Optionally, the sensing components are immobilized which allows their use to measure analytes in a moving stream.

For in vivo applications, the sensor is used in a moving stream of physiological fluid, preferably blood, which contains one or more polyhydroxyl organic compounds or is implanted in tissue such as muscle which contains said compounds. Therefore, it is preferred that none of the sensing moieties escape from the sensor assembly. Thus, for use in vivo, the sensing components are preferably part of an organic polymer sensing assembly. Soluble dyes and quenchers can be confined by a semi-permeable membrane that allows passage of the analyte but blocks passage of the sensing moieties. This can be realized by using soluble sensing moieties that are substantially larger than the analyte molecules (molecular weight of at least twice that of the analyte or greater than 1000 preferably greater than 5000); and employing a selectively semipermeable membrane such as a dialysis or an ultrafiltration membrane with a specific molecular weight cutoff between the two so that the sensing moieties are quantitatively retained.

Preferably the sensing moieties are immobilized in an insoluble polymer matrix, which is freely permeable to glucose. The polymer matrix is comprised of organic, inorganic or combinations of polymers thereof. The matrix may be composed of biocompatible materials. Alternatively, the matrix is coated with a second biocompatible polymer, and/or a semipermeable membrane, that is permeable to the analytes of interest.

The function of the polymer matrix is to hold together and immobilize the fluorescent dye and quencher moieties while at the same time allowing contact with the analyte, and binding of the analyte to the boronic acid. To achieve this effect, the matrix must be insoluble in the medium, and in close association with it by establishing a high surface area interface between matrix and analyte solution. For example, an ultra-thin film or microporous support matrix is used. Alternatively, the matrix is swellable in the analyte solution, e.g. a hydrogel matrix is used for aqueous systems. In some instances, the sensing polymers are bonded to a surface such as the surface of a light conduit, or impregnated in a microporous membrane. In all cases, the matrix must not interfere with transport of the analyte to the binding sites so that equilibrium can be established between the two phases. Techniques for preparing ultra-thin films, microporous polymers, microporous sol-gels, and hydrogels are established in the art. All useful matrices are defined as being analyte permeable.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. The compound:

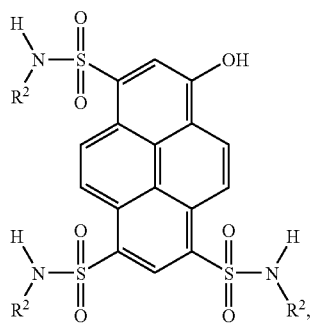

wherein:
$R^2$ is

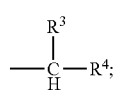

$R^3$ is $—(CH_2)_n—A^-M^+$,
  wherein n is 1-4,
  wherein $A^-$ is an anionic group selected from the group consisting of $SO_3^-$, $HPO_3^-$, $CO_2^-$ and

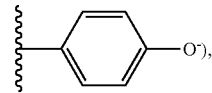

and
  wherein $M^+$ is a cationic group selected from the group consisting of $H^+$, an alkali metal ion, $Li^+$, $Na^+$, $K^+$, $Rb^+$, $Cs^+$, $Fr^+$, an onium ion and $NR_4^+$, wherein R is selected from the group consisting of alkyl, alkylaryl and aromatic groups);

$R^4$ is

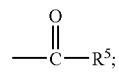

$R^5$ is selected from the group consisting of $$Y—(CH_2)_n—R^6 \quad \text{and} \quad Y—(\!(CH_2)_{n'}—O\!)_{\!n}\!(CH_2)_{\!n}\!—R^6,$$

wherein n is equal to 1-10, n' is equal to 2-4 and Y is selected from the group consisting of NH and O;
$R^6$ is selected from the group consisting of $NHR^7$, $OR^7$ and $CO_2H$; and
$R^7$ is H or an ethylenically unsaturated group selected from the group consisting of methacryloyl, acryloyl, styryl, acrylamido and methacrylamido.

2. The compound:

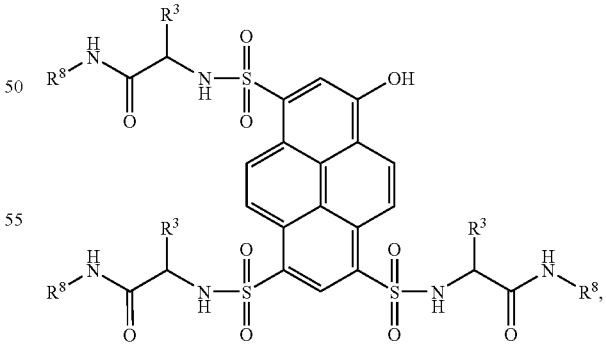

wherein:
$R^3$ is $—(CH_2)_n—A^-M^+$,
  wherein n is 1-4,
  wherein $A^-$ is an anionic group selected from the group consisting of $SO_3^-$, $HPO_3^-$, $CO_2^-$ and

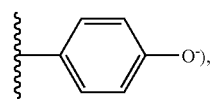

and wherein $M^+$ is a cationic group selected from the group consisting of $H^+$, an alkali metal ion, $Li^+$, $Na^+$, $K^+$, $Rb^+$, $Cs^+$, $Fr^+$, an onium ion and $NR_4^+$, wherein R is selected from the group consisting of alkyl, alkylaryl and aromatic groups);

$R^4$ is

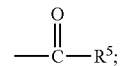

$R^8$ is selected from the group consisting of $-(CH_2)_n-R^9$ and $-(CH_2)_{n'}-O+CH_2+_n R^9$, wherein n is equal to 1-10, n' is equal to 2-4;
$R^9$ is selected from the group consisting of $NHR^{10}$, $OR^{10}$ and $CO_2H$; and
$R^{10}$ is H or an ethylenically unsaturated group selected from the group consisting of methacryloyl, acryloyl, styryl, acrylamido and methacrylamido.

3. The compound:

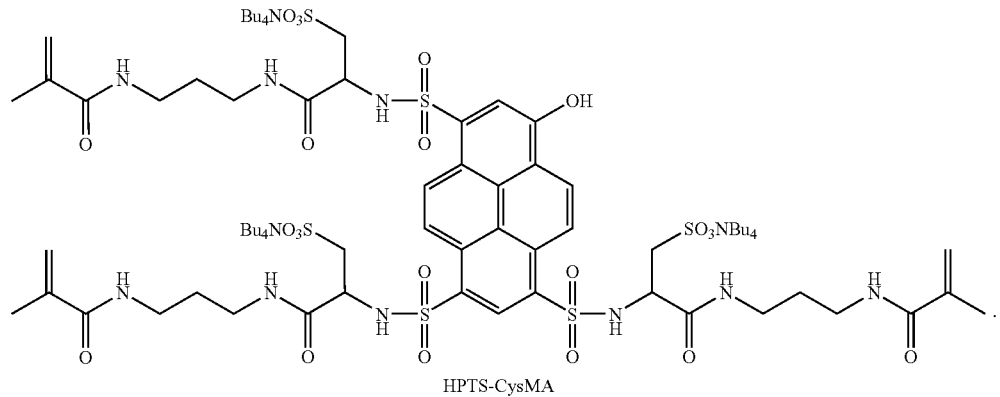

HPTS-CysMA

4. The compound of claim 3, wherein $NBu_4$ is any other counterion.

5. The compound of claim 3, comprising L, D, or L and D stereoisomers of cysteine.

6. A glucose sensor comprising the compound of claim 1.

7. The glucose sensor of claim 6, further comprising a quencher moiety.

8. The glucose sensor of claim 7, wherein said quencher moiety comprises boronic acid.

9. The glucose sensor of claim 8, wherein said boronic acid quencher is 3,3'-oBBV.

10. A method of making the compound of claim 1, comprising the steps of:

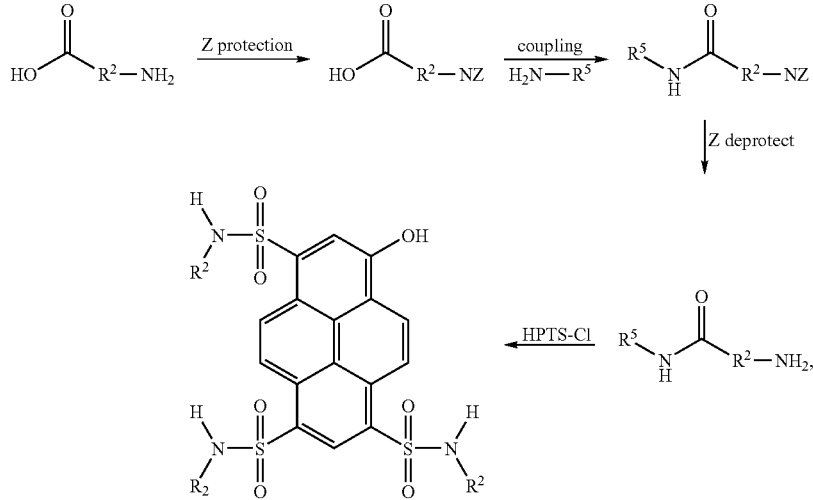

wherein:
R² is

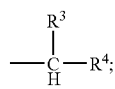

R³ is —(CH₂)ₙ—A⁻M⁺,
   wherein n is 1-4,
   wherein A⁻ is an anionic group selected from the group consisting of $SO_3^-$,
   $HPO_3^-$, $CO_2^-$ and

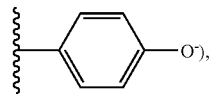

and wherein M⁺ is a cationic group selected from the group consisting of H⁺, an alkali metal ion, Li⁺, Na⁺, K⁺, Rb⁺, Cs⁺, Fr⁺, an onium ion and NR₄⁺, wherein R is selected from the group consisting of alkyl, alkylaryl and aromatic groups);
R⁴ is

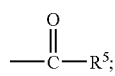

R⁵ is selected from the group consisting of $Y—(CH_2)_n—R^6$   and   $Y—[(CH_2)_{n'}—O]_n[CH_2]_n—R^6$, wherein n is equal to 1-10, n' is equal to 2-4 and Y is selected from the group consisting of NH and O;
R⁶ is selected from the group consisting of NHR⁷, OR⁷ and CO₂H;
R⁷ is H or an ethylenically unsaturated group selected from the group consisting of methacryloyl, acryloyl, styryl, acrylamido and methacrylamido; and
Z is an amino protecting group selected from the group consisting of Phthalimido, Boc and Fmoc.

11. A method of making the compound of claim 2, comprising the steps of:

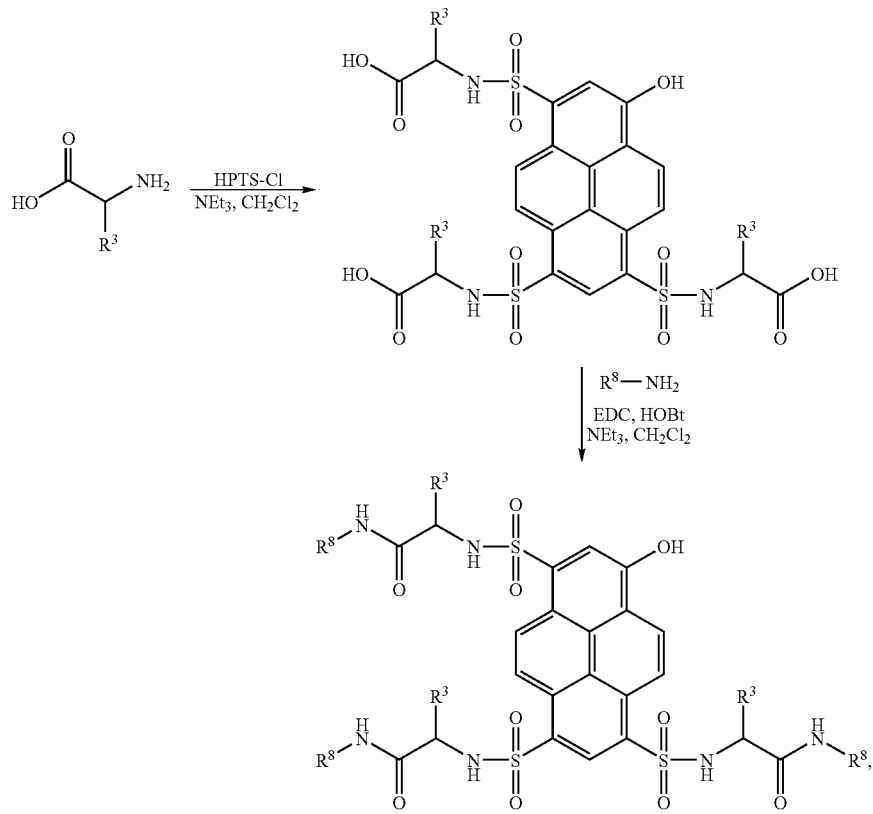

wherein:
R³ is —(CH₂)ₙ—A⁻M⁺,
   wherein n is 1-4,
   wherein A⁻ is an anionic group selected from the group consisting of $SO_3^-$,
   $HPO_3^-$, $CO_2^-$ and

and
wherein M+ is a cationic group selected from the group consisting of H+, an alkali metal ion, Li+, Na+, K+, Rb+, Cs+, Fr+, an onium ion and NR4+, wherein R is selected from the group consisting of alkyl, alkylaryl and aromatic groups);

$R^8$ is selected from the group consisting of

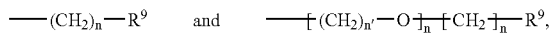

wherein n is equal to 1-10, n' is equal to 2-4;

$R^9$ is selected from the group consisting of $NHR^{10}$, $OR^{10}$ and $CO_2H$; and $R^{10}$ is H or an ethylenically unsaturated group selected from the group consisting of methacryloyl, acryloyl, styryl, acrylamido and methacrylamido.

12. A method of making the compound of claim 3, comprising the steps of making HPTS-CysOH as follows; and

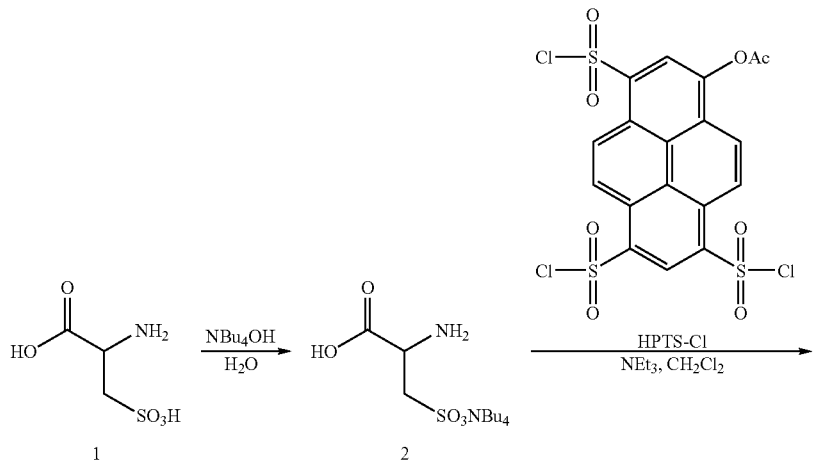

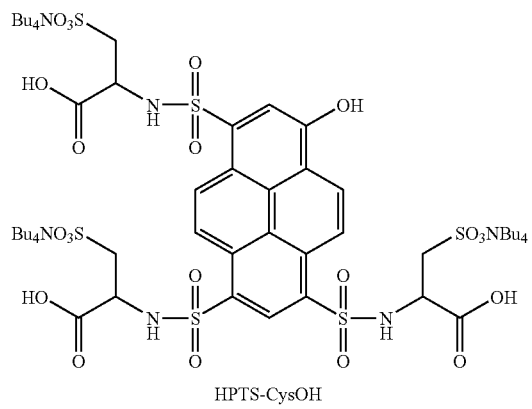

HPTS-CysOH making HPTS-Cys-MA as follows:
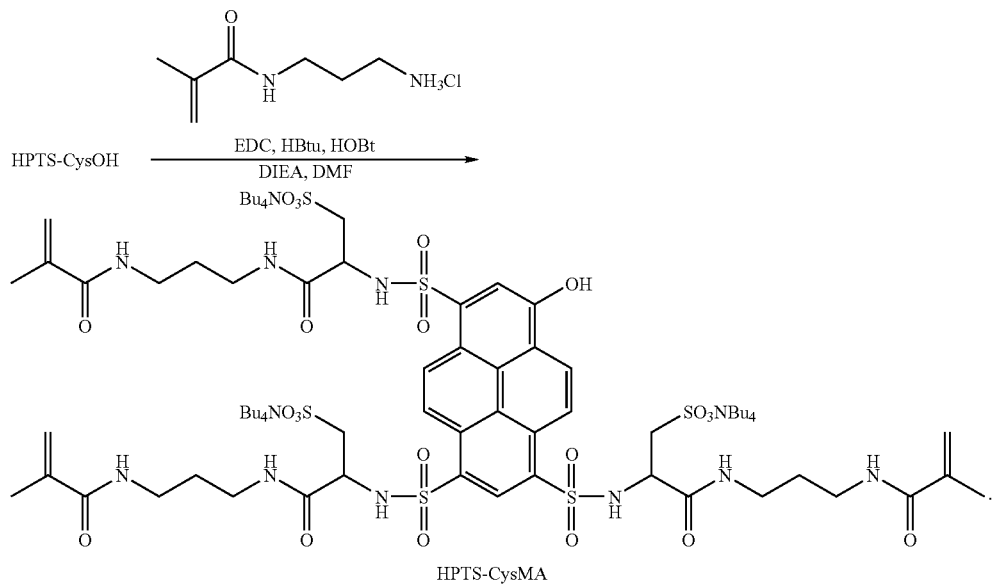
13. A method of making the compound of claim 3, comprising the steps of:
making TBCys as follows:
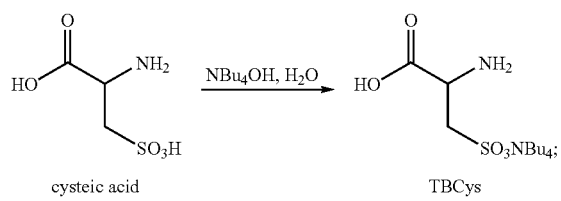
making Phth acid as follows:
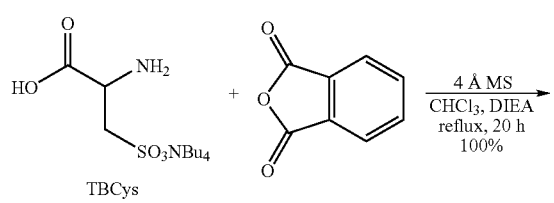
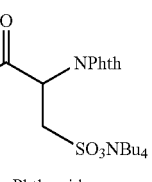
making Phth MA as follows:
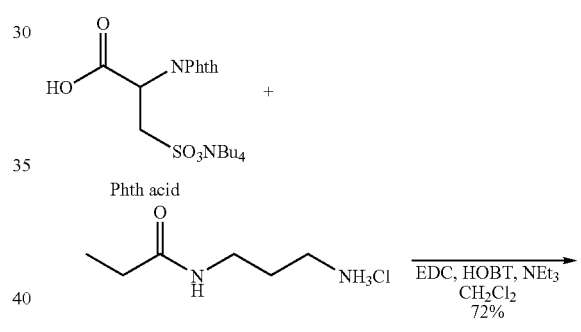
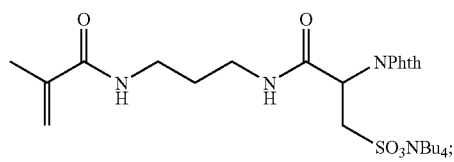
making AminoCysMA as follows:
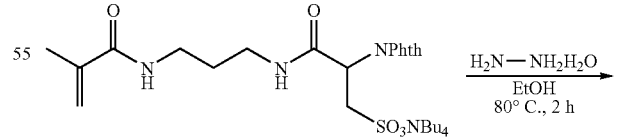
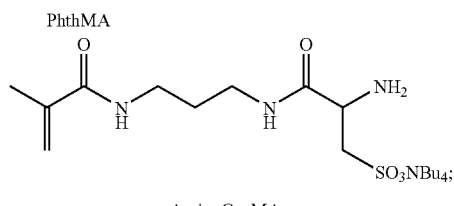

and making HPTS-Cys-MA as follows:
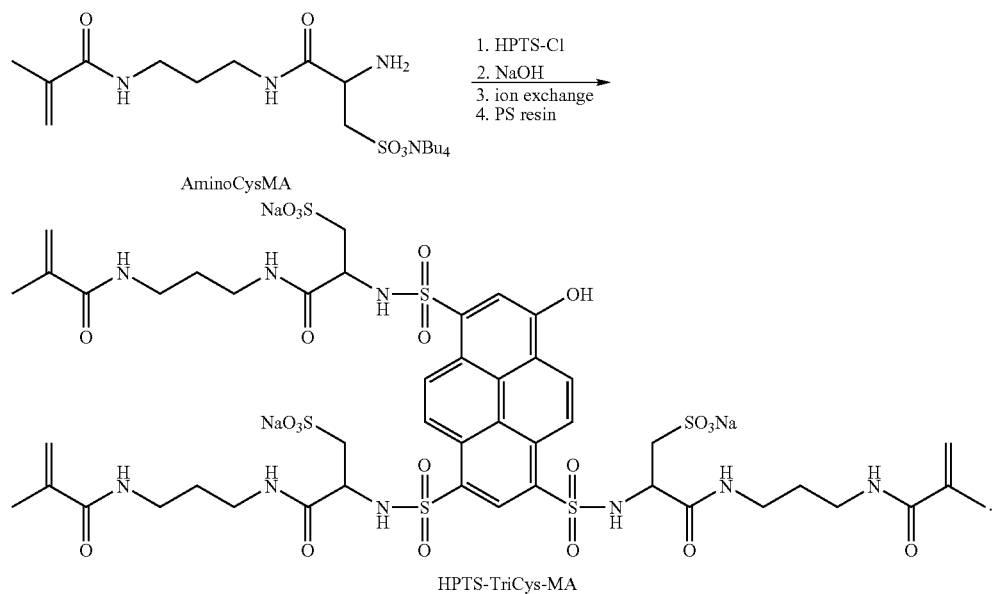
* * * * *

UNITED STATES PATENT AND TRADEMARK OFFICE
CERTIFICATE OF CORRECTION

PATENT NO. : 7,417,164 B2  Page 1 of 1
APPLICATION NO. : 11/782553
DATED : August 26, 2008
INVENTOR(S) : Jeff T. Suri It is certified that error appears in the above-identified patent and that said Letters Patent is hereby corrected as shown below:

At column 20, line 21-22, please delete "styryl,acrylamide" and insert therefore, -- styryl, acrylamide --.

At column 24, line 43, please delete "j=5.8" and insert therefore, -- J=5.8 --.

At column 27, line 17, please delete "B$_9$OH)$_2$" and insert therefore, -- B(OH)$_2$ --.

At column 28, line 11, please delete "Stem" and insert therefore, -- Stern --.

Signed and Sealed this

Second Day of June, 2009

JOHN DOLL
*Acting Director of the United States Patent and Trademark Office*